United States Patent [19]
Kinzler et al.

[11] Patent Number: 5,871,968
[45] Date of Patent: Feb. 16, 1999

[54] P21$^{WAF1}$ DERIVATIVES AND DIAGNOSTIC METHODS

[75] Inventors: Kenneth W. Kinzler, BelAir, Md.; Wafik El-Deiry, Philadelphia, Pa.; Bert Vogelstein, Baltimore, Md.

[73] Assignee: The Johns Hopkins University, Baltimore, Md.

[21] Appl. No.: 795,015

[22] Filed: Feb. 5, 1997

Related U.S. Application Data

[60] Division of Ser. No. 574,043, Dec. 18, 1995, and a continuation-in-part of Ser. No. 149,829, Nov. 10, 1993.

[51] Int. Cl.$^6$ .............................. C12N 15/63; C12N 5/10; C12N 15/09
[52] U.S. Cl. ................ 435/69.1; 435/320.1; 435/172.3; 435/375
[58] Field of Search .............................. 514/44; 424/93.2; 435/320.1, 325, 172.3, 69.1; 935/22, 33, 34

[56] References Cited

U.S. PATENT DOCUMENTS 5,302,706  4/1994  Smith ...................................... 536/23.1

FOREIGN PATENT DOCUMENTS

WO 92/13091  8/1992  WIPO.
WO 93/12251  6/1993  WIPO.

OTHER PUBLICATIONS

E. Marshall (1995) Science 269: 1050–1055.
Miller et al (1995) FASEB J. 9: 190–199.
R.G. Crystal (1995) Science 270: 404–410.
Chen et al., "Separate Domains of p21 Involved in the Inhibition of Cdk Kinase and PCNA" Nature 374:386–288 (1995).
El–Deiry et al., "WAF1, a Potential Mediator of p53", Cell 75:817–825 (1993).
El–Deiry et al., "Topological Control of p2$1^{WAF1/CIP1}$ Expression in Normal and Neoplastic Tissues", Cancer Research 55:291–2919 (1995).
Xiong et al., "p21 is a Universal Inhibitor of Cyclin Kinases", Nature 366:701–704 (1993).
Harper et al., "The p21 Cdk–Interacting Protein Cip1 is a Potent Inhibitor of G1 Cyclin–Dependent Kinases", Cell 75;805–816 (1993).
Zakut et al., The Tumor Suppression Function of p32$^{Waf}$ is Contained in its N–Terminal Half ('half–WAF'), Oncogene 11:393–395 (1995).

*Primary Examiner*—Jasemine C. Chambers
*Assistant Examiner*—Karen M. Hauda
*Attorney, Agent, or Firm*—Banner & Witcoff, Ltd.

[57] ABSTRACT

The striking compartmentalization of p21$^{WAF1}$ expression found in normal tissues is completely abrogated in neoplastic tissues. Methods are provided for using p21$^{WAF1}$ expression as a tool to assess neoplasia and to discover new drugs. A truncated p21$^{WAF1}$ protein is more active than full-length p21$^{WAF1}$ protein in inhibiting tumor cell growth.

4 Claims, 13 Drawing Sheets

FIG. 1b

| SITE DESIGNATION | SPECIES | 5' BOUNDARY RELATIVE TO TATA | —SEQUENCE— |
|---|---|---|---|
| SITE #1 (p53) | HUMAN | -2251 | GCTTTCTGGCCATCAGGAACATGTCCCAACATGTTG |
| | MOUSE | -2831 | GCTTTCTGGCCTTCAGGAACATGTCTTGACATGTTC |
| | RAT | -3213 | GCTTTCTGGCTTTCAGGAACATGTCTTGACTTGTTC |
| SITE #2 (p53) | HUMAN | -1344 | AGACTGGGCATGTCTGGGCA |
| | MOUSE | -1923 | AGACTGGGCATGTCTGGGCA |
| | RAT | -2256 | AGCCTGGGCATGTCTGGGCA |
| SITE #3 | HUMAN | -1701 | TTTTCTCCCAAAGTAAACAGAGACAATGTC |
| | MOUSE | -2263 | TTTTCTCCC-AAAGTAAACAGAGACAATGTC |
| | RAT | -2590 | TTTTCTCCC-AAAGTAAACAGAGACAATGTC |

1 2

200➤

69➤

30➤

21➤

14➤

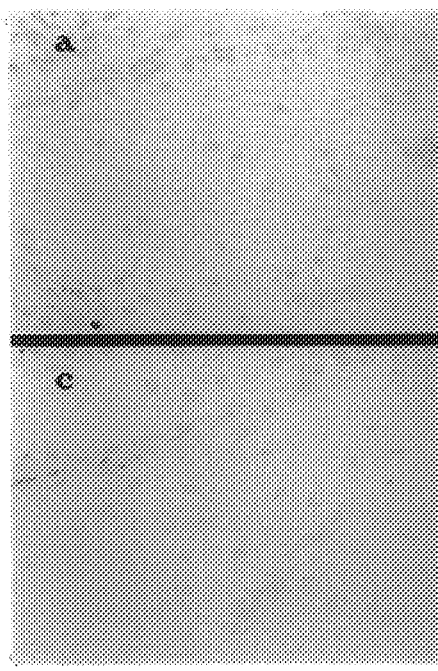 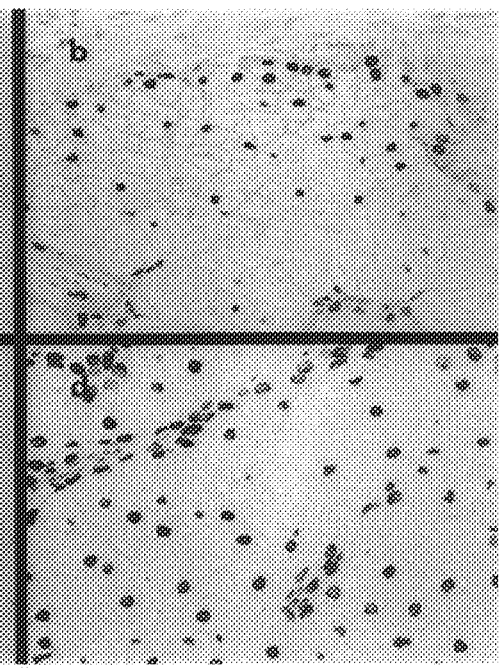
FIG. 4a    FIG. 4b
 
FIG. 4c    FIG. 4d

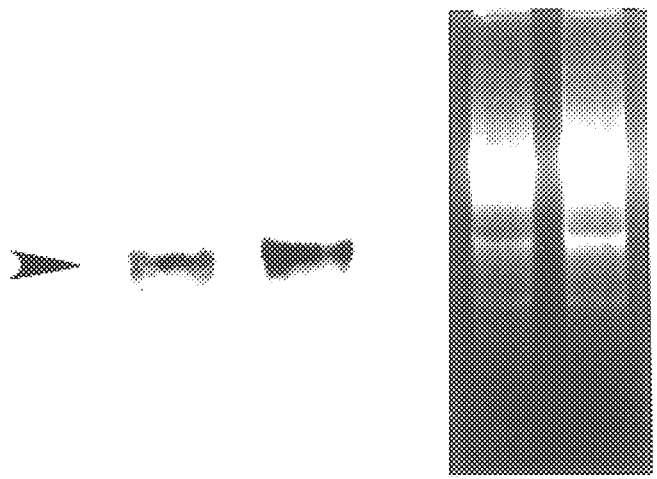

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
      ( A ) LENGTH: 2121 base pairs
      ( B ) TYPE: nucleic acid
      ( C ) STRANDEDNESS: double
      ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
      ( A ) ORGANISM: Homo sapiens
      ( H ) CELL LINE: GM ( v i i i ) POSITION IN GENOME:
      ( B ) MAP POSITION: 6p21.2

( i x ) FEATURE:
      ( A ) NAME/KEY: CDS
      ( B ) LOCATION: 76..568

( x i ) SEQUENCE DESCRIPTION: SEQ ID NO:1:

```
GCCGAAGTCA GTTCCTTGTG GAGCCGGAGC TGGGCGCGGA TTCGCCGAGG CACCGAGGCA                     60

CTCAGAGGAG GCGCC ATG TCA GAA CCG GCT GGG GAT GTC CGT CAG AAC CCA                     111
                Met Ser Glu Pro Ala Gly Asp Val Arg Gln Asn Pro
                 1               5                  10

TGC GGC AGC AAG GCC TGC CGC CGC CTC TTC GGC CCA GTG GAC AGC GAG                       159
Cys Gly Ser Lys Ala Cys Arg Arg Leu Phe Gly Pro Val Asp Ser Glu
         15                  20                  25

CAG CTG AGC CGC GAC TGT GAT GCG CTA ATG GCG GGC TGC ATC CAG GAG                       207
Gln Leu Ser Arg Asp Cys Asp Ala Leu Met Ala Gly Cys Ile Gln Glu
     30                  35                  40

GCC CGT GAG CGA TGG AAC TTC GAC TTT GTC ACC GAG ACA CCA CTG GAG                       255
Ala Arg Glu Arg Trp Asn Phe Asp Phe Val Thr Glu Thr Pro Leu Glu
 45                  50                  55                  60

GGT GAC TTC GCC TGG GAG CGT GTG CGG GGC CTT GGC CTG CCC AAG CTC                       303
```

|   |   |   |   |   |   |   |   |   |   |   |   |   |   |   |   |   |
|---|---|---|---|---|---|---|---|---|---|---|---|---|---|---|---|---|
| Gly | Asp | Phe | Ala | Trp<br>65 | Glu | Arg | Val | Arg | Gly<br>70 | Leu | Gly | Leu | Pro | Lys<br>75 | Leu | |

| TAC | CTT | CCC | ACG | GGG | CCC | CGG | CGA | GGC | CGG | GAT | GAG | TTG | GGA | GGA | GGC | 351 |
|---|---|---|---|---|---|---|---|---|---|---|---|---|---|---|---|---|
| Tyr | Leu | Pro | Thr<br>80 | Gly | Pro | Arg | Arg | Gly<br>85 | Arg | Asp | Glu | Leu | Gly<br>90 | Gly | Gly | |

| AGG | CGG | CCT | GGC | ACC | TCA | CCT | GCT | CTG | CTG | CAG | GGG | ACA | GCA | GAG | GAA | 399 |
|---|---|---|---|---|---|---|---|---|---|---|---|---|---|---|---|---|
| Arg | Arg | Pro<br>95 | Gly | Thr | Ser | Pro | Ala<br>100 | Leu | Leu | Gln | Gly | Thr<br>105 | Ala | Glu | Glu | |

| GAC | CAT | GTG | GAC | CTG | TCA | CTG | TCT | TGT | ACC | CTT | GTG | CCT | CGC | TCA | GGG | 447 |
|---|---|---|---|---|---|---|---|---|---|---|---|---|---|---|---|---|
| Asp | His<br>110 | Val | Asp | Leu | Ser | Leu<br>115 | Ser | Cys | Thr | Leu | Val<br>120 | Pro | Arg | Ser | Gly | |

| GAG | CAG | GCT | GAA | GGG | TCC | CCA | GGT | GGA | CCT | GGA | GAC | TCT | CAG | GGT | CGA | 495 |
|---|---|---|---|---|---|---|---|---|---|---|---|---|---|---|---|---|
| Glu<br>125 | Gln | Ala | Glu | Gly | Ser<br>130 | Pro | Gly | Gly | Pro | Gly<br>135 | Asp | Ser | Gln | Gly | Arg<br>140 | |

| AAA | CGG | CGG | CAG | ACC | AGC | ATG | ACA | GAT | TTC | TAC | CAC | TCC | AAA | CGC | CGG | 543 |
|---|---|---|---|---|---|---|---|---|---|---|---|---|---|---|---|---|
| Lys | Arg | Arg | Gln | Thr<br>145 | Ser | Met | Thr | Asp | Phe<br>150 | Tyr | His | Ser | Lys | Arg<br>155 | Arg | |

| CTG | ATC | TTC | TCC | AAG | AGG | AAG | CCC | T | AATCGCCCA | CAGGAAGCCT | 588 |
|---|---|---|---|---|---|---|---|---|---|---|---|
| Leu | Ile | Phe | Ser<br>160 | Lys | Arg | Lys | Pro | | | | |

| | | | | |
|---|---|---|---|---|
| GCAGTCCTGG | AAGCGCGAGG | GCCTCAAAGG | CCCGCTCTAC | ATCTTCTGCC | TTAGTCTCAG | 648 |
| TTTGTGTGTC | TTAATTATTA | TTTGTGTTTT | AATTTAAACA | CCTCCTCATG | TACATACCCT | 708 |
| GGCCGCCCCC | TGCCCCCCAG | CCTCTGGCAT | TAGAATTATT | TAAACAAAAA | CTAGGCGGTT | 768 |
| GAATGAGAGG | TTCCTAAGAG | TGCTGGGCAT | TTTTATTTTA | TGAAATACTA | TTTAAAGCCT | 828 |
| CCTCATCCCG | TGTTCTCCTT | TTCCTCTCTC | CCGGAGGTTG | GGTGGGCCGG | CTTCATGCCA | 888 |
| GCTACTTCCT | CCTCCCCACT | TGTCCGCTGG | GTGGTACCCT | CTGGAGGGGT | GTGGCTCCTT | 948 |
| CCCATCGCTG | TCACAGGCGG | TTATGAAATT | CACCCCCTTT | CCTGGACACT | CAGACCTGAA | 1008 |
| TTCTTTTTCA | TTTGAGAAGT | AAACAGATGG | CACTTTGAAG | GGGCCTCACC | GAGTGGGGGC | 1068 |
| ATCATCAAAA | ACTTTGGAGT | CCCCTCACCT | CCTCTAAGGT | TGGGCAGGGT | GACCCTGAAG | 1128 |
| TGAGCACAGC | CTAGGGCTGA | GCTGGGGACC | TGGTACCCTC | CTGGCTCTTG | ATACCCCCT | 1188 |
| CTGTCTTGTG | AAGGCAGGGG | GAAGGTGGGG | TACTGGAGCA | GACCACCCCG | CCTGCCCTCA | 1248 |
| TGGCCCCTCT | GACCTGCACT | GGGGAGCCCG | TCTCAGTGTT | GAGCCTTTTC | CCTCTTTGGC | 1308 |
| TCCCCTGTAC | CTTTTGAGGA | GCCCCAGCTT | ACCCTTCTTC | TCCAGCTGGG | CTCTGCAATT | 1368 |
| CCCCTCTGCT | GCTGTCCCTC | CCCCTTGTCT | TTCCCTTCAG | TACCCTCTCA | TGCTCCAGGT | 1428 |
| GGCTCTGAGG | TGCCTGTCCC | ACCCCCACCC | CCAGCTCAAT | GGACTGGAAG | GGGAAGGGAC | 1488 |
| ACACAAGAAG | AAGGGCACCC | TAGTTCTACC | TCAGGCAGCT | CAAGCAGCGA | CCGCCCCCTC | 1548 |
| CTCTAGCTGT | GGGGGTGAGG | GTCCCATGTG | GTGGCACAGG | CCCCCTTGAG | TGGGGTTATC | 1608 |
| TCTGTGTTAG | GGGTATATGA | TGGGGGAGTA | GATCTTTCTA | GGAGGGAGAC | ACTGGCCCCT | 1668 |
| CAAATCGTCC | AGCGACCTTC | CTCATCCACC | CCATCCCTCC | CCAGTTCATT | GCACTTTGAT | 1728 |
| TAGCAGCGGA | ACAAGGAGTC | AGACATTTTA | AGATGGTGGC | AGTAGAGGCT | ATGGACAGGG | 1788 |
| CATGCCACGT | GGGCTCATAT | GGGGCTGGGA | GTAGTTGTCT | TTCCTGGCAC | TAACGTTGAG | 1848 |
| CCCCTGGAGG | CACTGAAGTG | CTTAGTGTAC | TTGGAGTATT | GGGGTCTGAC | CCCAAACACC | 1908 |
| TTCCAGCTCC | TGTAACATAC | TGGCCTGGAC | TGTTTTCTCT | CGGCTCCCCA | TGTGTCCTGG | 1968 |
| TTCCCGTTTC | TCCACCTAGA | CTGTAAACCT | CTCGAGGGCA | GGGACCACAC | CCTGTACTGT | 2028 |
| TCTGTGTCTT | TCACAGCTCC | TCCCACAATG | CTGAATATAC | AGCAGGTGCT | CAATAAATGA | 2088 |
| TTCTTAGTGA | CTTTAAAAAA | AAAAAAAAAA | AAA | | | 2121 |

( 2 ) INFORMATION FOR SEQ ID NO:2:

( i ) SEQUENCE CHARACTERISTICS:
        ( A ) LENGTH: 164 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ser Glu Pro Ala Gly Asp Val Arg Gln Asn Pro Cys Gly Ser Lys
 1               5                  10                  15
Ala Cys Arg Arg Leu Phe Gly Pro Val Asp Ser Glu Gln Leu Ser Arg
                20                  25                  30
Asp Cys Asp Ala Leu Met Ala Gly Cys Ile Gln Glu Ala Arg Glu Arg
                35                  40                  45
Trp Asn Phe Asp Phe Val Thr Glu Thr Pro Leu Glu Gly Asp Phe Ala
                50                  55                  60
Trp Glu Arg Val Arg Gly Leu Gly Leu Pro Lys Leu Tyr Leu Pro Thr
 65                  70                  75                  80
Gly Pro Arg Arg Gly Arg Asp Glu Leu Gly Gly Arg Arg Pro Gly
                    85                  90                  95
Thr Ser Pro Ala Leu Leu Gln Gly Thr Ala Glu Glu Asp His Val Asp
                100                 105                 110
Leu Ser Leu Ser Cys Thr Leu Val Pro Arg Ser Gly Glu Gln Ala Glu
                115                 120                 125
Gly Ser Pro Gly Gly Pro Gly Asp Ser Gln Gly Arg Lys Arg Arg Gln
                130                 135                 140
Thr Ser Met Thr Asp Phe Tyr His Ser Lys Arg Arg Leu Ile Phe Ser
145                 150                 155                 160
Lys Arg Lys Pro
```

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( v i i i ) POSITION IN GENOME:
        ( B ) MAP POSITION: 6p21.2

( x i ) SEQUENCE DESCRIPTION: SEQ ID NO:3:

AGAATTGTCC TTTAT                                                    15

( 2 ) INFORMATION FOR SEQ ID NO:4:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO (iv) ANTI-SENSE: NO (vi) ORIGINAL SOURCE:
    (A) ORGANISM: Homo sapiens (viii) POSITION IN GENOME:
    (A) CHROMOSOME/SEGMENT: 6p21.2

(xi) SEQUENCE DESCRIPTION: SEQ ID NO:4:

GCTTTCTGGC CATCAGGAAC ATGTCCCAAC ATGTTG 36

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (viii) POSITION IN GENOME:
        (A) CHROMOSOME/SEGMENT: 6p.21.2

(xi) SEQUENCE DESCRIPTION: SEQ ID NO:5:

AGACTGGGCA TGTCTGGGCA 20

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (viii) POSITION IN GENOME:
        (A) CHROMOSOME/SEGMENT: 6p21.2

(xi) SEQUENCE DESCRIPTION: SEQ ID NO:6:

TTTTCTCCCC AAAGTAAACA GACAGACAAT GTC 33

(2) INFORMATION FOR SEQ ID NO:7:

(i) SEQUENCE CHARACTERISTICS:
        (A) LENGTH: 5143 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (H) CELL LINE: GM (viii) POSITION IN GENOME:
(A) CHROMOSOME/SEGMENT: 6p21.2

(xi) SEQUENCE DESCRIPTION: SEQ ID NO:7:

| | | | | | |
|---|---|---|---|---|---|
| GGATCCCTGT | AGAGATGCTC | AGGCTGCTGA | GGAGGGCGCG | GTGCTTGGTC | TCTATGAATA | 60 |
| CGATGACCTA | AAGCAAAAAA | AGAAGATGGC | TATGTCGGTG | AAGCTCTATG | GAACTGGGGA | 120 |
| TCAGGAGGCC | TGGCAGAAAG | GAGTCCTGTT | TGCTTCTGGG | CAGAACTTGG | CATGATGGAG | 180 |
| ACGCCAGCCA | GCGAGATGAT | GCCAACCAGA | TTTGCCGAAA | TTATTGAGAA | GAATCTCAAA | 240 |
| AGCCGCTAGT | AGTAAACCGA | GTTTCATATC | AGACCCAGGT | CTTGGATTGA | GGAACAGGCA | 300 |
| ATGGGATCAT | TCCTCAGTGT | GGCCAAAGGA | TCTGACGAGC | CCTCAGTCTT | CTTGGAAATT | 360 |
| CACTACATAG | GCAGCCCCAA | TGCAGACAAA | CCACCCCTTG | TTTGTTGGGA | AAGGAATTAC | 420 |
| CTTTGACAGT | GGTGGTATCT | CCATCAAGGC | TTCTGCAAAT | ATGGACCTCA | TGAGGGCCGA | 480 |
| CATGGGAGGA | GCTACAACTA | TATGCTCAGC | CATTGTGTCT | GCTGCAAATC | TCAGTTTGCC | 540 |
| CATTAATATT | ATAGGTCTGG | CCCCTCTGTG | AAAACATGCC | CAGCGGCAAG | GCCAACAAGC | 600 |
| TGGGGATGTT | GTTAGAGCCA | GGAACAGGAA | GACCATCCAG | GTTGGTAACA | CTGATGCTGA | 660 |
| GGGGAGGCTC | ATACTGGCTG | ATGCGCTCTG | TTACGTGCAC | ACATTTAACC | CGAAGGTCAT | 720 |
| CCTCAATGCC | ACCACCTTAA | CAGGTGTCAT | AGATGTAGCT | TTGGGGTCAG | GTGCCACTGG | 780 |
| GGTCTTTACC | AATTCATCCT | GGCTCTGGAA | CAAGCTCTTC | GAGGCCAGCA | TTGAAACAGG | 840 |
| GGACCGTGTC | TGGAGGATGC | CTCTCTTCAA | ACATTGTACA | AGACAGGTTG | TAGATTGCCA | 900 |
| GCTGGCTGAT | GTTAACAACA | TTGGAAAATA | TAGATCTGCG | GGAGCATGTA | CATCTGCGGC | 960 |
| ATTCCTGAAA | GAATTCGTGA | CTCATCCTAA | GTGGGCACAT | TTAGACATAG | CAGGTGTGAT | 1020 |
| GACCAACAAA | GATGAGGTTC | CCTATCTATG | GAAAGGCATG | ACCGGGAGGC | CCACAAGGAC | 1080 |
| TCTCATAGAG | TTCTTACTTC | GTTTCAGTCA | AGACAATGCT | TAGTTCAGAT | ACTCAAAAAA | 1140 |
| TGTCTTCACT | CTGTCTTAAA | TTGGACAGTT | GAAGTTAAAA | GGTTTTGAA | TGAATGGATG | 1200 |
| AAAATATTTT | AAAGGAGGCA | ATTTATATTT | AAAAATGTAG | AACACAATGA | AATTTTTATG | 1260 |
| CCTTGATTTT | TTTTTCATTT | TACACAAAGA | TTTATATATT | TTTTTTTTGA | GACGGAGTCT | 1320 |
| CACTCTGTCA | CCCAGGCTGG | AGTGCAGGTG | GCATGATCTC | AGCTCACTGC | AACCTCCGCC | 1380 |
| TCCTAGGTTC | AAGCGATTCT | CCCACCTCAG | CCACCTGAAT | ACCTGGGACT | ACAGGTGCCC | 1440 |
| ACCACCATGC | CCGGCTGATT | TTTGTATTTT | TAATGGAGAC | GGGGTTTCAC | CATATTGGCC | 1500 |
| AGGCTGGTCT | CAAAACTCCT | GACCCTGTGA | TCTGCCCGCC | TCGGCCTCCC | AAAGTGCTGG | 1560 |
| GATTACAGGC | GTAAACCACC | ACGCCCGGCC | AGTATATATT | TTTAATTGAG | AAGCAAAATT | 1620 |
| GTACTTCAGA | TTTGTGATGC | TAGGAACATG | AGCAAACTGA | AAATTACTAA | CCACTTGTCA | 1680 |
| GAAACAATAA | ATCCAACTTT | TTGTGCAAAA | AAAAAAAATA | CAAATATTAG | CTGGGCATGG | 1740 |
| TGGTGCATGC | CTGTAATCCC | AGCTACTCGG | GAGGCTGAGG | CAGAATTGCT | TGAACCTGGG | 1800 |
| AGGCGGAGAC | TGCAGTGAGC | TGAGATTGTG | CCACTGCTGA | CTTTGTCTCA | AAAACAAAA | 1860 |
| CAAAACAAAA | AAACAAAATG | AAAACAAAAA | GCCAGGGCTG | CCTCTGCTCA | ATAATGTTCT | 1920 |
| ATCTTTGTTC | CGCCTCTTCT | CTGGGGTCTC | ACTTCTTGGG | AGCCTGTGTG | AAGGTGAATT | 1980 |
| CCTCTGAAAG | CTGACTGCCC | CTATTTGGGA | CTCCCAGTC | TCTTTCTGAG | AAATGGTGAC | 2040 |
| ATTGTTCCCA | GCACTTCCTC | TCCCTTCCTA | GGCAGCTTCT | GCAGCCACCA | CTGAGCCTTC | 2100 |
| CTCACATCCT | CCTTCTTCAG | GCTTGGGCTT | TCCACCTTTC | ACCATTCCCC | TACCCCATGC | 2160 |
| TGCTCCACCG | CACTCTGGGG | AGGGGGCTGG | ACTGGGCACT | CTTGTCCCCC | AGGCTGAGCC | 2220 |

-continued

```
TCCCTCCATC CCTATGCTGC CTGCTTCCCA GGAACATGCT TGGGCAGCAG GCTGTGGCTC    2280
TGATTGGCTT TCTGGCCATC AGGAACATGT CCCAACATGT TGAGCTCTGG CATAGAAGAG    2340
GCTGGTGGCT ATTTTGTCCT TGGGCTGCCT GTTTTCAGGG AGGAAGGGGA TGGTAGGAGA    2400
CAGGAGACCT CTAAAGACCC CAGGTAAACC TTAGCCTCTT ACTCTGAACA GGGTATGTGA    2460
TCTGCCAGCA GGATCCTTGC GACAGGGCTG GGATCTGATG CATGTGTGCT TGTGTGAGTG    2520
TGTGCTGGGA GTCAGATTCT GTGTGTGACT TTTAACAGCC TGCTCCCTTG CCTTCTTCAG    2580
GGCAGAAGTC CTCCCTTAGA GTGTGTCTGG GTACACATTC AAGTGCATGG TTGCAAACTT    2640
TTTTTTTTAA AGCACTGAAT AGTACTAGAC ACTTAGTAGG TACTTAAGAA ATATTGAATG    2700
TCGTGGTGGT GGTGAGCTAG AAGTTATAAA AAAAATTCTT TCCCAAAAAC AACAACAAAA    2760
AGAATTATTT CATTGTGAAG CTCAGTACCA CAAAAATTCA TTACAATAAT TCATTACAAG    2820
CCTTTATTAA AAAAAATTTT CTCCCCAAAG TAAACAGACA GACAATGTCT AGTCTATTTG    2880
AAATGCCTGA AAGCAGAGGG GCTTCAAGGC AGTGGGAGAA GGTGCCTGTC CTCTGCTGGA    2940
CATTTGACAA CCAGCCCTTT GGATGGTTTG TATGTATAGG AGCGAAGGTG CAGACAGCAG    3000
TGGGGCTTAG AGTGGGGTCC TGAGGCTGTG CTGTGGCCCT TCTGGGGTTT AGCCACAATC    3060
CTGGCCTGAC TCCAGGGCGA GGCAGGCCAA GGGGGTCTGC TGCTGTGTCC TCCCACCCCT    3120
ACCTGGGCTC CCATCCCCAC AGCAGAGGAG AAAGAAGCCT GTCCTCCCCG AGGTCAGCTG    3180
CGTTAGAGGA AGAAGACTGG GCATGTCTGG GCAGAGATTT CCAGACTCTG AGCAGCCTGA    3240
GATGTCAGTA ATTGTAGCTG CTCCAAGCCT GGGTTCTGTT TTTCAGTGGG ATTTCTGTTC    3300
AGATGAACAA TCCATCCTCT GCAATTTTTT AAAAGCAAAA CTGCAAATGT TTCAGGCACA    3360
GAAAGGAGGC AAAGGTGAAG TCCAGGGGAG GTCAGGGGTG TGAGGTAGAT GGGAGCGGAT    3420
AGACACATCA CTCATTTCTG TGTCTGTCAG AAGAACCAGT AGACACTTCC AGAATTGTCC    3480
TTTATTTATG TCATCTCCAT AAACCATCTG CAAATGAGGG TTATTTGGCA TTTTTGTCAT    3540
TTTGGAACCA CAGAAATAAA GGATGACAAG CAGAGAGCCC CGGGCAGGAG GCAAAAGTCC    3600
TGTGTTCCAA CTATAGTCAT TTCTTTGCTG CATGATCTGA GTTAGGTCAC CAGACTTCTC    3660
TGAGCCCCAG TTTCCCCAGC AGTGTATACG GGCTATGTGG GGAGTATTCA GGAGACAGAC    3720
AACTCACTCG TCAAATCCTC CCCTTCCTGG CCAACAAAGC TGCTGCAACC ACAGGGGTTT    3780
CTTCTGTTCA GGTGAGTGTA GGGTGTAGGG AGATTGGTTC AATGTCCAAT TCTTCTGTTT    3840
CCCTGGAGAT CAGGTTGCCC TTTTTTGGTA GTCTCTCCAA TTCCTCCTT CCCGGAAGCA     3900
TGTGACAATC AACAACTTTG TATACTTAAG TTCAGTGGAC CTCAATTTCC TCATCTGTGA    3960
AATAAACGGG ACTGAAAAAT CATTCTGGCC TCAAGATGCT TTGTTGGGGT GTCTAGGTGC    4020
TCCAGGTGCT TCTGGGAGAG GTGACCTAGT GAGGGATCAG TGGGAATAGA GGTGATATTG    4080
TGGGGCTTTT CTGGAAATTG CAGAGAGGTG CATCGTTTTT ATAATTTATG AATTTTTATG    4140
TATTAATGTC ATCCTCCTGA TCTTTTCAGC TGCATTGGGT AAATCCTTGC CTGCCAGAGT    4200
GGGTCAGCGG TGAGCCAGAA AGGGGCTCA TTCTAACAGT GCTGTGTCCT CCTGGAGAGT     4260
GCCAACTCAT TCTCCAAGTA AAAAAAGCCA GATTTGTGGC TCACTTCGTG GGAAATGTG     4320
TCCAGCGCAC CAACGCAGGC GAGGGACTGG GGGAGGAGGG AAGTGCCCTC CTGCAGCACG    4380
CGAGGTTCCG GGACCGGCTG GCCTGCTGGA ACTCGGCCAG GCTCAGCTGC TCCGCGCTGG    4440
GCAGCCAGGA GCCTGGGCCC CGGGGAGGGC GGTCCCGGGC GGCGCGGTGG GCCGAGCGCG    4500
GGTCGCCTCC TTGAGGCGGG CCCGGGCGGG GCGGTTGTAT ATCAGGGCCG CGCTGAGCTG    4560
CGCCAGCTGA GGTGTGAGCA GCTGCCGAAG TCAGTTCCTT GTGGAGCCGG AGCTGGGCGC    4620
```

-continued

```
GGATTCGCCG  AGGCACCGAG  GCACTCAGAG  GAGGTGAGAG  AGCGGCGGCA  GACAACAGGG   4680

GACCCCGGGC  CGGCGGCCCA  GAGCCGAGCC  AAGCGTGCCC  GCGTGTGTCC  CTGCGTGTCC   4740

GCGAGGATGC  GTGTTCGCGG  GTGTGTGCTG  CGTTCACAGG  TGTTTCTGCG  GCAGGTGAAT   4800

GACGGGCGTG  GGTCGGTGCG  CGCTCGGCTT  GCGCACACGG  TGTCTCTAAG  TGCGCGGGTG   4860

ACGAGGGTCG  GGATGTGCCG  GAGACCCCGG  GCGGAGAGCG  GGATTACAAG  TACAGGAATC   4920

CCTGGCCACG  CTCCCCGCCC  CTGGAAACCC  AGCTGGGGCG  AGGGAGGGCG  TGGACGGGAC   4980

CGTTCTGGGA  GCTCGCCTTT  GGCTGCGGTT  GGCTCCAGGC  CCCAGGCGCA  GTTTGCTCGC   5040

GGCGTGGGGA  TGAAGTCCGT  GTCCCTGGAG  GGGCCCAGGA  AGGGCGAGGA  AAGCGGAGTG   5100

GAGTAAGTTC  GTCTAGGATC  GGTCCCGGGT  GGCTCTGGGA  TCC                      5143
```

P21$^{WAF1}$ DERIVATIVES AND DIAGNOSTIC METHODS

This application is a divisional of application Ser. No. 08/574,043 filed on Dec. 18, 1995, now pending, and a continuation-in-part of Ser. No. 08/149,829, filed Nov. 10, 1993, now pending.

The U.S. Government has a paid-up license in this invention and the right in limited circumstances to require the patent owner to license others on reasonable terms as provided for by the terms of grant GM07184, CA43460, and CA62924 awarded by the National Institutes of Health.

BACKGROUND OF THE INVENTION

The cell cycle and the genetic alterations that drive tumorigenesis are inextricably linked. Examples include the amplification of cyclin and cyclin dependent kinase (CDK) genes, the phosphorylation of Rb by CDK'S, the control of the CDK inhibitor p21$^{WAF1}$ by p53, and the tumor suppressor activity of the CDK inhibitor p16 (reviewed by Sherr, 1994, Hunter and Pines, 1994).

A turning point in cell cycle research was realized with the discovery that cyclin complexes had different constitutions in transformed and nontransformed cells (Xiong et al., 16992, Xiong et al., 1993). In particular, the complexes in the non-transformed cells were associated with small proteins different from those found in transformed derivatives. A variety of approaches subsequently determined that these small proteins not only bound to the cyclin complexes, but were potent inhibitors of the associated CDK's (p21: Harper et al., 1993, Xiong et al., 1993b, Gu et al., 1993, p16: Serrano et al., 1993, p15: Hannon and Beach, 31994, p18: Guan et al., 1994, p27: Polyak et al, 1994, Toyoshima and Hunter, 1994).

Five CDK inhibitors have thus far been identified. The first to be cloned, p21$^{WAF1}$ (also known as CIP1, SDI1, MDA6, CAP20), is encoded by a gene on chromosome 6p and can be directly regulated by p53 (El-Deiry et al., 1993). It inhibits a broad range of cyclin-CDK complexes, and may be involved in cellular senescence as well as in neoplasia (Noda et al., 1994). In vitro, p21$^{WAF1}$ also complexes with the proliferating cell nuclear antigen (PCNA), resulting in an inhibition of DNA replication (Li et al., 1994, Flores-Rozas et al., 1994). A related gene, p27$^{KIP1}$, is located on chromosome 12p and may play a role in a subset of leukemias (Bullrich et al., 1995, Pietenpol et al., 1995, Ponce-Castaneda et al., 1995). The p16, p15 and p18 genes are unrelated to the p21/p27 family, and have a more selective inhibitory activity, affecting only CDK4 and 6. The p16 and p15 genes are homozygously deleted in many human cancers, and p16 mutations result in familial melanoma (Kamb et al., 1994 a,b, Nobori et al., 1994, Hussussian et al., 1994, Jen et al., 1994).

Although cell culture studies have been used to initially study these CDK inhibitors, such studies fail to provide insight into their regulation in intact animals. There is a continuing need in the art for methods and reagents for diagnosing and treating cancer patients. An understanding of in vivo regulation can lead to new diagnostic and therapeutic tools.

SUMMARY OF THE INVENTION

It is an object of the invention to provide forms of p21$^{WAF1}$ protein which are more active in tumor suppression than wild-type p21$^{WAF1}$.

It is another object of the invention to provide cDNA, vectors, and host cells for production of more active forms of p21$^{WAF1}$.

It is another object of the invention to provide a method for distinguishing neoplastic from non-neoplastic tissues.

It is another object of the invention to provide a method for diagnosis of gastrointestinal cancers.

It is another object of the invention to provide a method of inhibiting p21$^{WAF1}$ expression in a cell.

It is yet another object of the invention to provide a method for supplying a gene function to a cell which expresses p21$^{WAF1}$.

It is still another object of the invention to provide a method for screening potential therapeutic agents for the ability to suppress or stimulate the growth of cells by regulating the expression of p21$^{WAF1}$.

These and other objects of the invention are provided by one or more of the embodiments described below. In one embodiment of the invention a truncated p21$^{WAF1}$ protein is provided which consists of less than 164 amino acids and consists of at least the N-terminal 78 amino acids as shown in SEQ ID NO:2, wherein said truncated p21$^{WAF1}$ protein is more active than full-length p21$^{WAF1}$ protein in inhibiting tumor cell growth.

In another embodiment of the invention a cDNA segment is provided which encodes a truncated p21$^{WAF1}$ protein which consists of less than 164 amino acids and consists of at least the N-terminal 78 amino acids as shown in SEQ ID NO: 2, wherein said truncated p21$^{WAF1}$ protein is more active than full-length p21$^{WAF1}$ protein in inhibiting tumor cell growth.

In yet another embodiment of the invention a cDNA segment is provided which consists of the coding sequence shown in SEQ ID NO: 1, with a termination codon in a position between codons 78 and 164.

In still another embodiment of the invention a method of distinguishing neoplastic cells from non-neoplastic cells is provided. The method comprises the steps of:

staining immunohistochemically a human colonic epithelial tissue comprising colonic crypts with an antibody which specifically immunoreacts with p21$^{WAF1}$;

observing a pattern of stained and unstained cells, wherein a neoplastic tissue is identified when less than 25% of the colonic crypts are stained.

In yet another embodiment of the invention, a method of distinguishing neoplastic cells from non-neoplastic cells is provided. The method comprises the steps of:

staining immunohistochemically a human colonic epithelial tissue comprising colonic crypts with a first antibody which specifically immunoreacts with p21$^{WAF1}$ and with a second antibody which specifically immunoreacts with a marker of replication;

observing a pattern of stained and unstained cells, wherein a neoplastic tissue is identified: (1) when a mixture of (a) cells displaying p21$^{WAF1}$ staining, and (b) cells displaying the marker of replication staining, is observed at the surface of the colonic crypts; or (2) when no distinct boundary is observed between cells displaying p21$^{WAF1}$ staining and cells displaying the marker of replication staining.

In another embodiment, a method of inhibiting p21$^{WAF1}$ expression in a cell by competing for transcription activation factors is provided. The method comprises administering a population of DNA molecules comprising a p21$^{WAF1}$ transcriptional regulatory region to a cell which expresses p21$^{WAF1}$.

In another embodiment, a method of supplying a gene function to a cell which expresses p21$^{WAF1}$ is provided. The method comprises administering to the cell a construct comprising a p21$^{WAF1}$ transcription regulatory region covalently linked in a cis configuration to a gene encoding the gene function, whereby said gene is expressed in said cell and said gene function is supplied to said cell.

In another embodiment, a method for screening potential therapeutic agents for the ability to suppress or stimulate the growth of cells by inhibiting the expression of p21$^{WAF1}$ is provided. The method comprises the steps of:

incubating a potential therapeutic agent with a cell which contains a p21$^{WAF1}$ reporter construct, said reporter construct comprising a p21$^{WAF1}$ transcription regulatory region covalently linked in a cis configuration to a gene encoding an assayable product;

measuring the production of the assayable product, and identifying a potential therapeutic agent which increases or decreases the production by the cell of the assayable product. Such an agent may suppress or stimulate the growth of tumor cells by activating or inhibiting the expression of p21$^{WAF1}$.

In another embodiment, a method of prescreening therapeutic agents for use in regulating the growth of cells by regulating the expression of p21$^{WAF1}$ is provided. The method comprises the steps of:

measuring in the presence of a test substance binding of (a) a protein which specifically binds to a p21$^{WAF1}$ transcription regulatory region to (b) a DNA molecule sequence selected from the group consisting of nucleotides 17–36 of SEQ ID NO: 4, nucleotides 1–15 of SEQ ID NO: 3, nucleotides 1–36 of SEQ ID NO: 4, nucleotides 1–20 of SEQ ID NO: 5, nucleotides 1–33 of SEQ ID NO: 6, and nucleotides 1–5143 of SEQ ID NO: 7;

measuring binding of said protein to said DNA molecule in the absence of a test substance; and comparing the measured binding of said protein in the presence of said test substance to the measured binding of said protein in the absence of said test substance, a test substance which increases or decreases the amount of binding being a candidate for use in regulating the growth of cells.

In another embodiment, a method of prescreening therapeutic agents in vitro for use in regulating the growth of cells by regulating the expression of p21$^{WAF1}$ is provided. The method comprises the steps of:

measuring in vitro transcription from a transcription construct, said transcription construct comprising a reporter gene which encodes an assayable product and a p21$^{WAF1}$ transcription regulatory sequence selected from the group consisting of nucleotides 17–36 of SEQ ID NO: 4, nucleotides 1–15 of SEQ ID NO: 3, nucleotides 1–36 of SEQ ID NO: 4, nucleotides 1–20 of SEQ ID NO: 5, nucleotides 1–33 of SEQ ID NO: 6, and nucleotides 1–5143 of SEQ ID NO: 7, said p21$^{WAF1}$ transcription regulatory sequence being upstream from and adjacent to said reporter gene, said in vitro transcription being effected in the presence and absence of a test substance;

determining whether transcription of said reporter gene is altered by the presence of said test substance, a test substance which alters the transcription of said reporter gene being a candidate for use in regulating the growth of cells.

In still another embodiment, a method of prescreening oligonucleotides for use in regulating the growth of tumor cells is provided. The method comprises the steps of:

adding (a) a p53 protein which is encoded by a mutant gene found in a cancer patient and (b) a preparation of mixed oligonucleotides to (c) a DNA fragment comprising a p21$^{WAF1}$ transcription regulatory region wherein said DNA fragment is immobilized on a solid support, to bind said p53 protein to said DNA fragment immobilized on a solid support, wherein said DNA fragment contains a double stranded sequence selected from the group consisting of nucleotides 17–36 of SEQ ID NO: 4, nucleotides 1–15 of SEQ ID NO: 3, nucleotides 1–36 of SEQ ID NO: 4, nucleotides 1–20 of SEQ ID NO: 5, nucleotides 1–33 of SEQ ID NO: 6, and nucleotides 1–5143 of SEQ ID NO: 7; wherein said p53 protein does not bind to said DNA fragment in the absence of said oligonuleotides; and recovering oligonucleotides from said preparation which bound to said p53 protein which bound to said DNA fragment immobilized on the solid support.

The present invention thus provides the art with improved tools for management of cancers.

BRIEF DESCRIPTION OF THE DRAWINGS

The file of this patent contains at least one drawing executed in color.

FIGS. 1a–d provide an analysis of the p21$^{WAF1}$/CIP1 promoter. FIG. 1a shows the arrangement of sites 1, 2, and 3 in human, mouse, and rat with respect to the TATA box. FIG. 1b shows the sequence of sites 1–3 in the three species. Arrows indicate the p53-binding consensus tetrameres. Asterisks indicate nucleotide positions that are not conserved among the three species. FIG. 1c shows the binding of sites 1 and 2 to wild-type (wt) and mutant p53 proteins. Mutant binding sites contained substitutions at position 4 of the pentamer. FIG. 1d shows p53-dependent transcriptional activity of deletion constructs. All constructs contained the transcription start site, TATA box (designated as position 1), and varying amounts of promoter sequence, as indicated. The level of p53-dependent CAT activity was defined as the activity at 32° C. (wt p53) divided by that at 37° C. (mutant p53 conformation).

FIG. 4 shows p21$^{WAF1}$ expression in sebaceous glands. Expression of p53 (FIG. 4a) or p21$^{WAF1}$ (FIG. 4b) was detected using the D07 and EA10 antibodies, respectively. In situ DNA fragmentation analysis was carried out either in the absence (FIG. 4c) or presence (FIG. 4d) of terminal deoxynucleotidyl transferase.

FIG. 7 demonstrates northern blot analysis of $p21^{WAF1}$ in p53 −/− (lane 1) and +/+ (lane 2) mouse colonic crypts. Crypts were isolated and RNA purified from them. An autoradiogram depicting the hybridization is shown on the left, and the corresponding ethidium bromide stain of the RNA, showing equivalent loading, is shown on the right.

FIG. 8 shows loss of topological control in benign colonic tumors.

DETAILED DESCRIPTION OF THE PREFERRED EMBODIMENTS

Figure 1A:
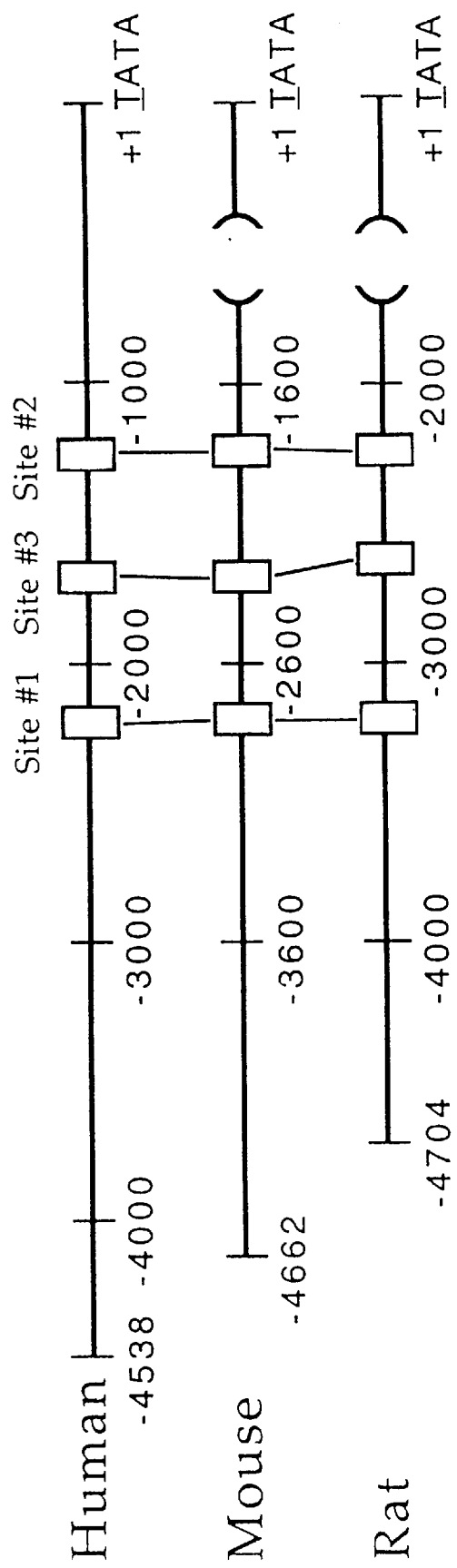

It is a discovery of the present invention that there is a striking compartmentalization of $p21^{WAF1}$ expression which correlates with cellular proliferation rather than differentiation. In neoplastic tissues, particularly in colonic neoplasms, this distinct compartmentalization is completely abrogated. Thus cell cycle inhibitors are normally subject to precise topological control, and escape from this regulation is a critical feature of neoplastic transformation. Furthermore, it is a discovery of the present invention that there is a global decrease in $p21^{WAF1}$ expression in neoplastic tissues.

The compartmentalization of $p21^{WAF1}$ expression in normal tissues occurs throughout the gastrointestinal tract including colon, small intestine, stomach, and esophagus. Expression of $p21^{WAF1}$ is confined to the post-replicative or nonproliferating compartment, including the upper half of the crypts, surface epithelium, and the gastric pits in oxyntic gastric mucosa. Replicative or proliferating compartments can be identified by expression of marker(s) of replicating cells. Markers of replication are known and commonly used in the art, such as proteins that are specifically synthesized during S phase e.g., PCNA and Ki67.

Expression of $p21^{WAF1}$ and markers of replicating or proliferating cells occurs in a mutually exclusive pattern. In a given tissue, replication marker expression is found in one part of the tissue and abruptly stops where $p21^{WAF1}$ expression begins. A boundary is seen between the two types of cells. The distinct separation between compartments expressing $p21^{WAF1}$ and replication markers observed in normal tissues changes to a random expression pattern of both $p21^{WAF1}$ and replication markers in neoplastic tissues. The boundary separating the expression of $p21^{WAF1}$ and replication markers is unrecognizable.

In normal colonic crypts, Ki67 (or other replication marker) is expressed in cells near the base of the colonic crypt and extends about half way up the crypt columns; $p21^{WAF1}$ expression begins where Ki67 expression stops and continues up to the lumen. Neoplastic colonic crypts demonstrate a random mix of $p21^{WAF1}$ and Ki67—expressing cells at the surface of the colonic crypts. Disappearance of the boundary separating $p21^{WAF1}$ and Ki67 expression indicates neoplasia.

Expression of $p21^{WAF1}$ and markers of replicating or proliferating cells is readily detectable by techniques available in the field. These include immunohistochemical methods, in situ hybridization, Northern blot. Other methods that can reveal the level of a particular mRNA or protein can be used. Detection of expression of $p21^{WAF1}$ and proliferation markers in the same sample specimen can be achieved by double staining with more than one antibody using immunohistochemical methods. In one preferred embodiment, $p21^{WAF1}$ expression in human tissues can be detected by immunohistochemical staining with antibodies specifically immunoreactive with $p21^{WAF1}$. In another preferred embodiment, anti-Ki67 antibody and a monoclonal anti-$p21^{WAF1}$ antibody are used sequentially or simultaneously to double stain the sample. Immunohistochemical methods for staining human neoplastic or non-neoplastic tissues are well known in the art. Any such technique can be used.

Figure 2:
FIG. 2 demonstrates the specificity of the anti-p21$^{WAF1}$ monoclonal antibody. Western analysis is shown of GM cell lysates, either in the absence (lane 1) or presence (lane 2) of dexamethasone, using the EA10 antibody. The sizes of co-electrophoresed molecular weight markers are shown on the left, in kDa.

Antibodies used may be polyclonal or monoclonal and may be raised using any protein containing $p21^{WAF1}$ epitopes as immunogens, including native $p21^{WAF1}$ protein, or $p21^{WAF1}$ fusion proteins. The antibodies should be immunoreactive with $p21^{WAF1}$ epitopes, preferably epitopes not present on other human proteins. In a preferred embodiment of the invention, the antibodies will detect $p21^{WAF1}$ proteins in paraffin or frozen tissue sections, using immunocytochemical techniques. Techniques for raising and purifying antibodies are well known in the art and any such techniques may be employed. In one preferred embodiment, the monoclonal antibody EA10 is used. It shows strong reactivity to denatured $p21^{WAF1}$ protein, with no cross-reacting proteins visible on Western blot analysis (FIG. 2). This antibody is also noteworthy for its ability to recognize $p21^{WAF1}$ via immunohistochemical methods.

Expression of $p21^{WAF1}$ can be quantified through several methods known in the art. In one embodiment, one can determine the distribution and levels of the immunohistochemical staining in the sample and compare it with that of normal control. A global decrease in $p21^{WAF1}$ expression compared to normal is indicative of neoplasia. In a preferred embodiment, neoplastic tissue is identified when a ratio of expression in sample to normal control of less than 25% is observed.

Expression of p21$^{WAF1}$ can be inhibited by supplying to a cell expressing p21$^{WAF1}$, a population of DNA molecules comprising a p21$^{WAF1}$ transcription regulatory region which is disclosed in SEQ ID NO: 3, 4, 5, 6, or 7. The population of DNA molecules can be delivered to the cell in the form of double-stranded DNA fragment or within a vector. Modifications to DNA fragments or vectors may be desirable to increase the uptake by cells or to decrease nuclease sensitivity. All such modifications are within the contemplation of the invention.

Expression of p21$^{WAF1}$ can also be used in gene therapy to achieve expression in cells in which p21$^{WAF1}$ is normally expressed. It is well within the ability of one skilled in the art to make a construct containing a DNA coding sequence of a gene of interest and a p21$^{WAF1}$ transcriptional regulatory region upstream of the coding sequence, so that the gene will be expressed in cells in which p21$^{WAF1}$ is normally expressed. The p21$^{WAF1}$ transcription regulatory region is disclosed in SEQ ID NO: 3, 4, 5, 6, or 7.

Protein p21$^{WAF1}$ is the prototype of a family of small proteins that negatively regulate the cell cycle. Surprisingly, we have found that derivatives of p21$^{WAF1}$, particularly a truncated p21$^{WAF1}$ protein, can be more active than full-length p21$^{WAF1}$ protein in inhibiting tumor cell growth. In one preferred embodiment, a truncated protein including at least the N-terminal 78 amino acids as shown in SEQ ID NO: 2 is provided. It is more active than full-length p21$^{WAF1}$ protein in inhibiting tumor cell growth. Truncated proteins of the invention may have at least 88, 98, 108, 118, or 128 amino acids of p21$^{WAF1}$. Similarly other truncated forms having from 78 to 163 amino acids of p21$^{WAF1}$ may be used. Although applicants do not wish to be limited by any particular theory of operation, it is believed that a portion of the protein in the C-terminal half limits the tumor inhibiting activity of the protein.

Methods for making truncated proteins are well known in the art. One can, for example, synthesize a cDNA segment encoding the truncated protein by PCR amplification using a full length p21$^{WAF1}$ cDNA as a template and primers which amplify less than the full length protein. Such a cDNA segment can be put into an expression vector, either fused in frame with another protein or by itself. Alternatively, one can directly subclone the desired cDNA segment encoding a truncated protein into an expression vector by restriction enzyme digestion. Alternatively, the DNA can be mutagenized to create a premature termination codon. Any known technique for making a DNA segment encoding a truncated p21$^{WAF1}$ protein can be applied. Numerous DNA expression vectors and suitable host cells are known or commercially available. It is well within the ability of one skilled in the art to choose among known DNA expression vectors and the host cells that are compatible with the DNA vectors. In addition, procedures for isolating and purifying a truncated protein or a fusion protein including the truncated protein are well known, and any of these procedures can be applied in this invention. The techniques for PCR amplification, cloning and subcloning are also well known in the art and any such techniques may be chosen to achieve the preparation of the invention.

Screening methods have been devised to isolate chemical agents which may have use in therapy. Agents can be screened for the ability to affect the binding of protein factors that bind to a transcriptional regulatory region of p21$^{WAF1}$. Known factors which bind to the transcriptional regulatory region and regulate the expression of p21$^{WAF1}$ include wild-type and mutant p53 protein and MyoD.

According to one method, the ability of a test substance or a potential therapeutic agent to stimulate or inhibit the growth of cells is assessed via measuring the activity of a reporter construct. One such prescreening method is an in vitro transcription assay in which the transcription of a reporter gene is measured. In particular, the transcriptional activity of a reporter gene is measured in the presence or absence of protein factors known to bind a transcriptional regulatory region of p21$^{WAF1}$. Methods for measuring transcriptional activity in vitro can be any which are known in the art. Kits for carrying out in vitro transcription are commercially available from several companies. Alternatively, the expression of a reporter gene in a cell is measured. A reporter construct comprises a reporter gene or a gene encoding a convenient assayable enzyme activity, such as chloramphenicol acetyltransferase or β-galactosidase, and a transcriptional regulatory region of p21$^{WAF1}$ covalently linked in a cis configuration 5' of the reporter gene. A potential therapeutic agent which increases the production of the assayable product in the cell or the transcription of the reporter gene in vitro indicates its ability to increase the expression of p21$^{WAF1}$ and subsequently inhibit the growth of the cell. Similarly, a test substance which decreases the production of the assayable product in the cell or the transcription of the reporter gene in vitro indicates its ability to decrease the expression of p21$^{WAF1}$ and subsequently stimulate the growth of the cell.

According to another method, an in vitro binding assay is used. The amount of binding of a protein factor to a DNA molecule which comprises a transcriptional regulatory region of p21$^{WAF1}$ is measured in the presence and absence of a test substance. If incubation with the test substance increases or decreases the amount of binding, then the test substance is a candidate for use in regulating the growth of cells. This method can be used as a prescreening method to identify candidate therapeutic agents.

Methods for measuring amount of binding of proteins to DNA can be any which are known in the art. See, for example, Tan and Richmond, Cell, vol. 62, pp. 367–377 (1990). One particular method employs immunoprecipitation. Briefly, purified protein factor or a lysate of a cell expressing the protein factor is incubated with radiolabeled DNA and antibodies raised against the protein factor under conditions where proteins bind to DNA. Protein A-sepharose and poly-dIdC-poly-dIdC is then added for an additional incubation. A pellet is formed and washed and the proteins are removed by digestion with a protease and phenol extraction. The immunoprecipitated DNA is then analyzed by electrophoresis and quantified. Quantitation of the DNA can be by autoradiography, for example. The amount of DNA immunoprecipitated is proportional to the strength of binding of the protein factor to the DNA, where the DNA is in excess.

According to still another method, agents especially oligonucleotides can be screened for the ability to affect the structure of mutant p53 molecules so that their ability to bind specific-DNA-binding sites immobilized on a solid support and their ability to bind and/or transactivate at specific-DNA-binding sites are restored. The necessary components for such a screening method are provided by this invention and include DNA molecules which contain a sequence selected from the group consisting of nucleotides from SEQ ID NO: 3, 4, 5, 6, or 7. Mutant p53 proteins found in tumors are well known in the art. Not all mutations in p53 destroy specific-DNA-binding ability. For example, mutations in phosphorylation sites of p53 have been made and tested; they retain binding activity. However, such mutations have never been found in tumors. Mutations in p53 which are found in tumors are termed oncogenic herein and are employed in the method. Double-stranded DNA fragments which comprise a p21$^{WAF1}$ transcription regulatory region, as described above, are attached to an insoluble polymeric support. The support may be agarose, cellulose, polycarbonate, polystyrene and the like.

The following examples are provided for exemplification purposes only and are not intended to limit the scope of the invention which has been described in broad terms above.

EXAMPLE 1

Cell Lines and Tissues

The GM cell line was obtained from Ed Mercer (Mercer et al., 1990). REF-112 cells were obtained from Moshe Oren (Michalovitz et al., 1990). normal human tissues were obtained from the Department of Pathology of The Johns Hopkins Hospital or from Biogenex Laboratories, San Ramon, Calif. p53 −/− and +/+ mice were obtained from Genpharm, Palo Alto, Calif.

EXAMPLE 2

Monoclonal Antibodies

Female (Balb/c×C57BI/6) F1 mice were immunized by intraperitoneal injection of purified GST-WAF1 fusion protein in Ribi adjuvant (Ribi Immunochem Research, Inc.). The fusion protein, containing amino acids 1 to 164 of p21$^{WAF1}$, was expressed as an insoluble protein in *E. coli*, collected by centrifugation following cell lysis by passage through a French pressure cell (SLM Instruments), and purified by electroelution using SDS/PAGE. Hybridomas were produced as described (Smith et al., 1993), except that test bleeds and hybridomas were screened by ELISA for anti-p21$^{WAF1}$ reactivity using GST-p21$^{WAF1}$ and GST-MDM2 coated microtiter plates. Hybridoma supernatants which were positive by ELISA were tested by immunoblot using lysates of GM cells treated with dexamethasone to induce p53-dependent p21$^{WAF1}$ expression as described (El-Deiry et al., 1993). Five hybridomas were isolated which appeared to specifically detect p21$^{WAF1}$ and were subcloned twice by limiting dilution. Monoclonal antibody EA10, isotype IgG1, gave the strongest signal in immunoblotting and immunostaining of p21$^{WAF1}$ and was chosen for further study.

The D07 anti-p53 monoclonal antibody was obtained from Novacastra, Newcastle upon Tyne, UK. Clone MIB-1 anti-Ki67 monoclonal antibody was obtained from Immunotech, Westbrook, Me. The GM cell line contains a wild-type p53 gene whose expression is inducible by dexamethasone (Mercer et al., 1990). Little p21$^{WAF1}$ expression is observed in GM cells in the absence of dexamethasone, but in its presence, intense reactivity confined to the nucleus is observed.

EXAMPLE 3

UV Treatment of Human Skin

It has been demonstrated that DNA-damaging agents cause a substantial increase in p53 expression (Kastan et al., 1992, Lu and Lane, 1993, Campbell et al., 1993). The increased p53 is soon followed by the induction of p21$^{WAF1}$, at least in vitro (Dulic et al., 1994, El-Deiry et al., 1994). To determine whether this regulatory circuit functions in vivo, volunteers were exposed to low doses of ultraviolet (UV) radiation, and skin biopsies were obtained and examined for their P53 and P21$^{WAF1}$ expression.

Biopsies of skin were obtained from the lower back of healthy male volunteers, with informed consent, following UV radiation as previously described (Campbell et al., 1993). The UV source was an irradiation monochromator (Applied Photophysics Ltd, Surrey, UK, model UV90) optically coupled to a high pressure Zenon arc lamp with a central wavelength of 300 nm and a band width of +/−5 nm. Doses ranged between 2.5–112 mJ/cm2 and erythemal intensities were measured using a reflectance instrument (Campbell et al., 1993). Biopsies were taken from normal unirradiated skin, skin with no visibly perceptible erythema (sub minimal erythema dose) and skin with an erythema index nearest to 0.1 above base line. As an additional control, comparisons were made with sites covered with sunscreen prior to irradiation (Sun E45 SPF 25 containing 18% titanium dioxide; Crookes Healthcare, Nottingham, UK). Biopsies were taken 24 hours following irradiation, fixed in paraformaldehyde, embedded in paraffin, and sectioned for immunohistochemical analysis.

Figures 3A, 3B, 3C, 3D, 3E, 3F:
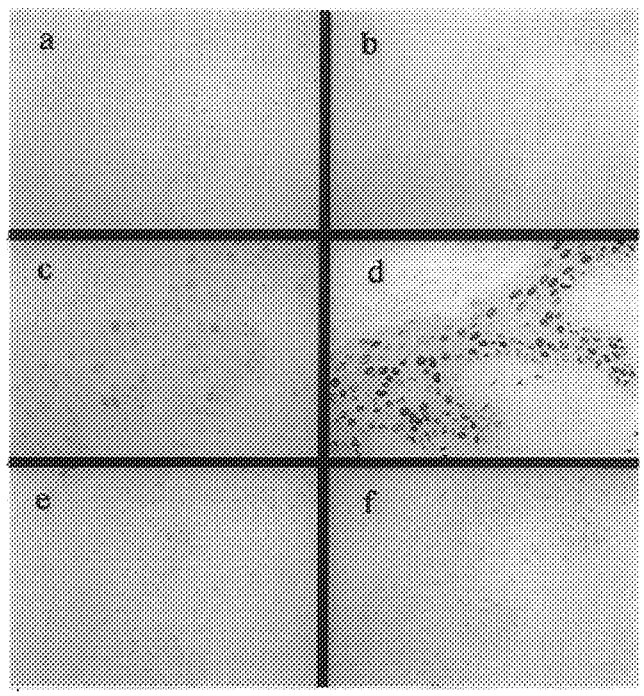
FIG. 3 shows the UV induction of p21$^{WAF1}$ protein in vivo. Human skin was either untreated (FIG. 3a and 3b), or treated (FIGS. 3c, 3d, 3e, and 3f) with UV light either without (FIGS. 3c and 3d) or with (FIGS. 3e and 3f) pretreatment with sunscreen. Sections were analyzed for p53 (FIGS. 3a, 3c, and 3e), or p21$^{WAF1}$ (FIGS. 3b, 3d, and 3f) expression, using immunohistochemical methods.
Figures 5A, 5B, 5C:
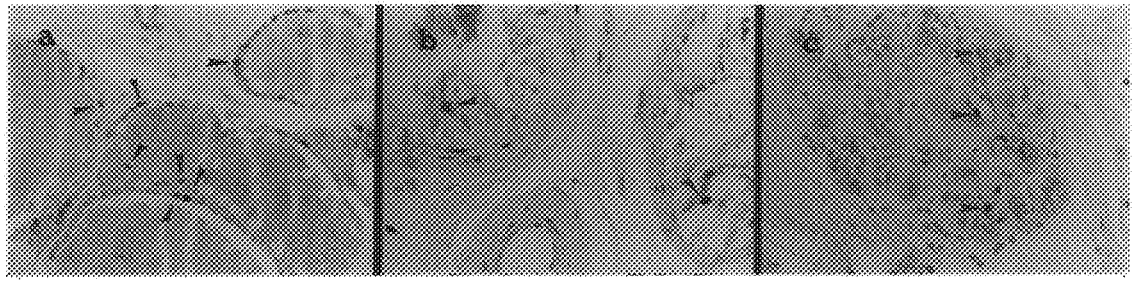
FIG. 5 demonstrates p21$^{WAF1}$ expression in adult human tissues. The EA10 monoclonal antibody was used to detect p21$^{WAF1}$ expression in thyroid (FIG. 5a), testes (FIG. 5b), breast (FIG. 5c), prostate (FIG. 5d), uterus (FIG. 5e), stomach (FIG. 5f), tongue (FIG. 5g), kidney (FIG. 5h), and colon (FIG. 5i). Arrow heads indicate some of the p21$^{WAF1}$ expressing nuclei.
Figures 5D, 5E, 5F:
Figures 5G, 5H, 5I:
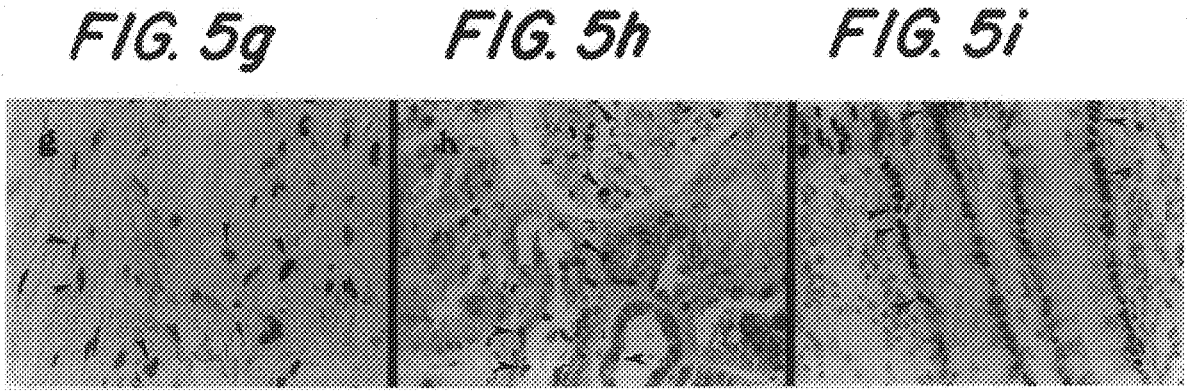

In the absence of radiation, little p53 or p21$^{WAF1}$ expression was detectable (FIG. 3*a*, 3*b*). Following irradiation, marked increases in both p53 and p21$^{WAF1}$ expression were observed (FIG. 3*c*, 3*d*). As in vitro, p21$^{WAF1}$ expression was localized to the nucleus. The dependence of this response on UV light is documented by its absence when skin is pretreated with sunscreen (FIG. 3*e*, 3*f*).

EXAMPLE 4

Analysis of p21$^{WAF1}$ Regulatory Region

It is previously demonstrated that p21$^{WAF1}$ expression can be transcriptionally regulated by wild-type p53 (El-Deiry et al., 1993). However, p21$^{WAF1}$ can also be regulated in a p53-independent manner (Michieli et al., 1994, Parker et al., 1995, Halevy et al., 1995, Zhang et al., 1995). The sequence of the human p21$^{WAF1}$ gene upstream of the coding region was determined and compared to analogous sequences of the mouse and rat. Because the structure, function, and p53 inducibility of p21$^{WAF1}$ is conserved among these three species, the important regulatory elements should also be conserved.

Figure 1C:
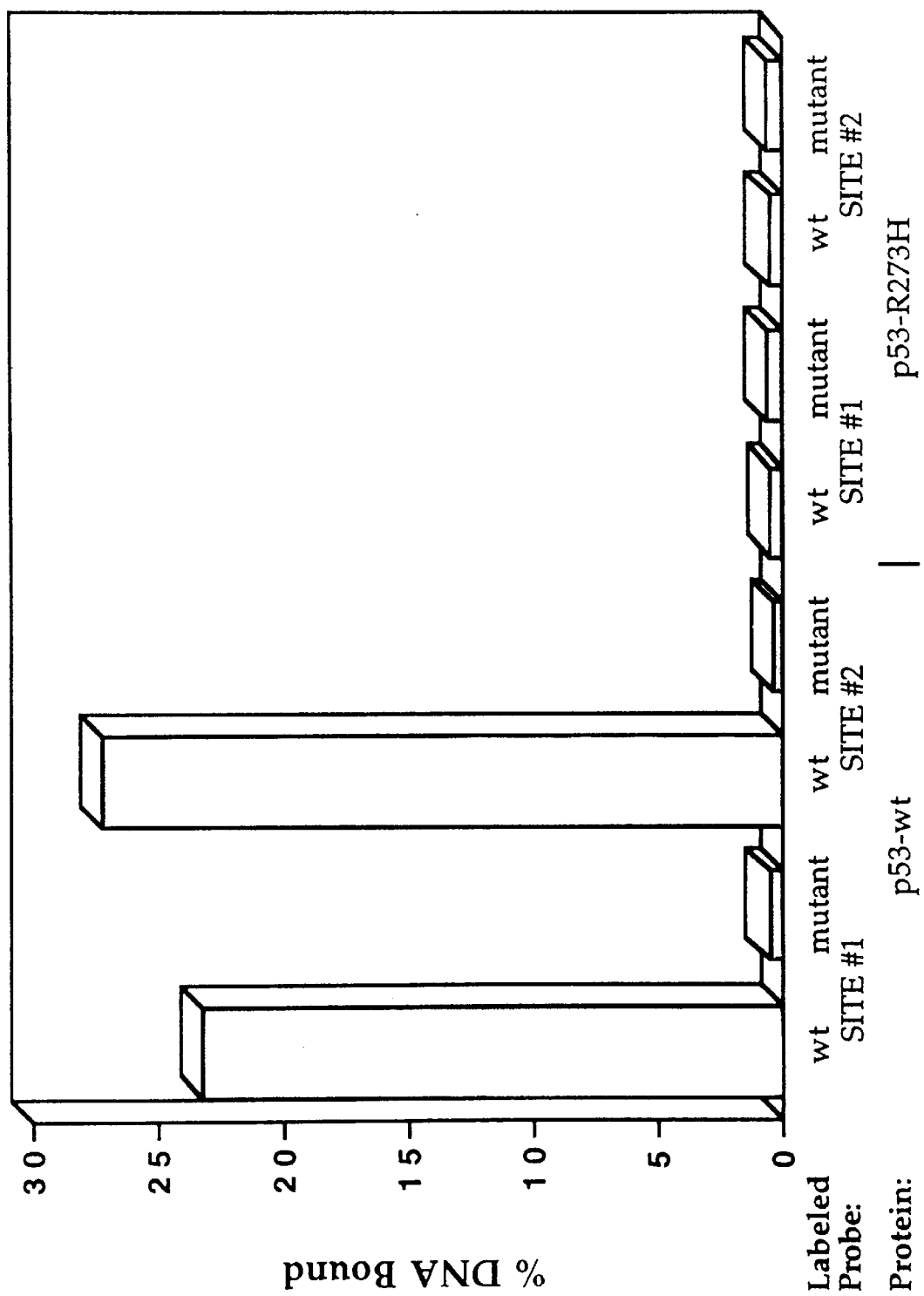

The amino acid sequences of rat and mouse p21$^{WAF1}$ are 90% identical to each other, and 75% identical to human p21$^{WAF1}$. The sequences upstream of the coding region, however, are remarkably divergent. Even when compare for short regions of conserved sequence, only a few stretches of homology were observed within the 4.5 kb of sequence determined for each species. The longest of these were three 20–36 bp blocks located 1.3, 1.7, and 2.2 kb upstream of the first exon of human p21$^{WAF1}$. These sites were not only conserved in sequence, but also in relative position (FIG. 1*a*, 1*b*). For example, there were 891 bp separating Sites 1 and 2 in the human, and 6892 bp separating these sites in the mouse. Two of these three sites (Site 1 and Site 2) contained p53 recognition elements, consisting of four tandem PuPuPuC(A/T) pentamers (El-Deiry et al., 1992, Funk et al., 1992). Site 1 had been identified previously in a screen for sequences that could confer p53 inducibility to reporter genes in *S. cerevisiae* (El-Deiry et al., 1993). Both these sites bound to wt p53, as determined by immunoprecipitation assays, but they did not bind to mutant p53 protein (FIG. 1*c*). When the C residues at position 4 of each p53 binding site consensus pentamer were substituted with A residues, the sites no longer bound to wt p53 (FIG. 1*c*).

A series of deletion constructs was generated to determine the relationship of these sites to p53 inducibility. In each case, a segment of the p21$^{WAF1}$ gene encompassing the beginning of the transcribed sequences and various lengths of upstream sequence was placed adjacent to a CAT reporter gene. These constructs were transfected into rat fibroblasts containing a temperature sensitive (ts) p53 gene and assayed for expression at the permissive (32° C., wt p53) and nonpermissive (39° C., mutant p53) temperatures (Michalovitz et al., 1990).

A BamHI restriction endonuclease digest of the P1-WAF1 clone was analyzed by Southern blot, and the region upstream of human p21$^{WAF1}$ was identified as a 4.5 kb BamHI fragment. The fragment was cloned and its sequence determined from clones generated by transposon insertion (Devine and Boeke, 1994). The human p21$^{WAF1}$ promoter deletion-CAT reporters were constructed by first PCR-amplifying progressively smaller segments of the region upstream of the p21$^{WAF1}$ gene, and then subcloning into pJFCAT1 (Fridovich-Keil et al., 1991). In order to obtain the mouse and rat p21$^{WAF1}$ promoters, we first isolated the mouse and rat p21$^{WAF1}$ cDNA's by probing appropriate cDNA libraries with the human cDNA at low stringency. The sequences of these cDNA clones was used to design primers for PCR screening of mouse and rat genomic P1 libraries (Genome Systems, St. Louis, Mo.). Restriction fragments containing 4.6 kb (mouse) and 4.7 kb (rat) of the p21$^{WAF1}$ upstream region were subcloned into the pJFCAT1 vector, and their sequence determined with the aid of nested deletions, generated by exonuclease Il1 and mung bean exonuclease digestion. Transfections and CAT assays were performed as previously described (Kern et al., 1992).

The DNA binding immunoprecipitation assays were performed as described (El-Deiry et al., 1992), except that binding was quantitated by liquid scintillation counting of the $^{32}$P-labeled immune complexes. DNA fragments tested for binding were generated by PCR amplification of Sites 1 and 2 from the rat promoter. Site 1 contained nt −3273 to −3112 and Site 2 contained nt −2333 to −2160 relative to the TATA box. Mutated sites 1 and 2 (see FIG. 1c) were comprised of PCR-generated fragments of the same length as the wt sites, but with substitutions at position 4 of the p53-recognizing pentamers. Thus, mutant site 1 contained the sequence 5'-GGAATATATCTTGAATTCTTC-3', and mutant Site 2 contained the sequence 5'-ATCCTGGGAATTTCTGGGAA-3' at positions corresponding to nt −3194 to −3178 and nt −2255 to −2236, respectively. The promoter sequences of human, rat, and mouse p21$^{WAF1}$ were compared to each other by using a computer program designed to detect any contiguous identities of 7 bp or greater, regardless of position within the promoter.

Figure 1D:
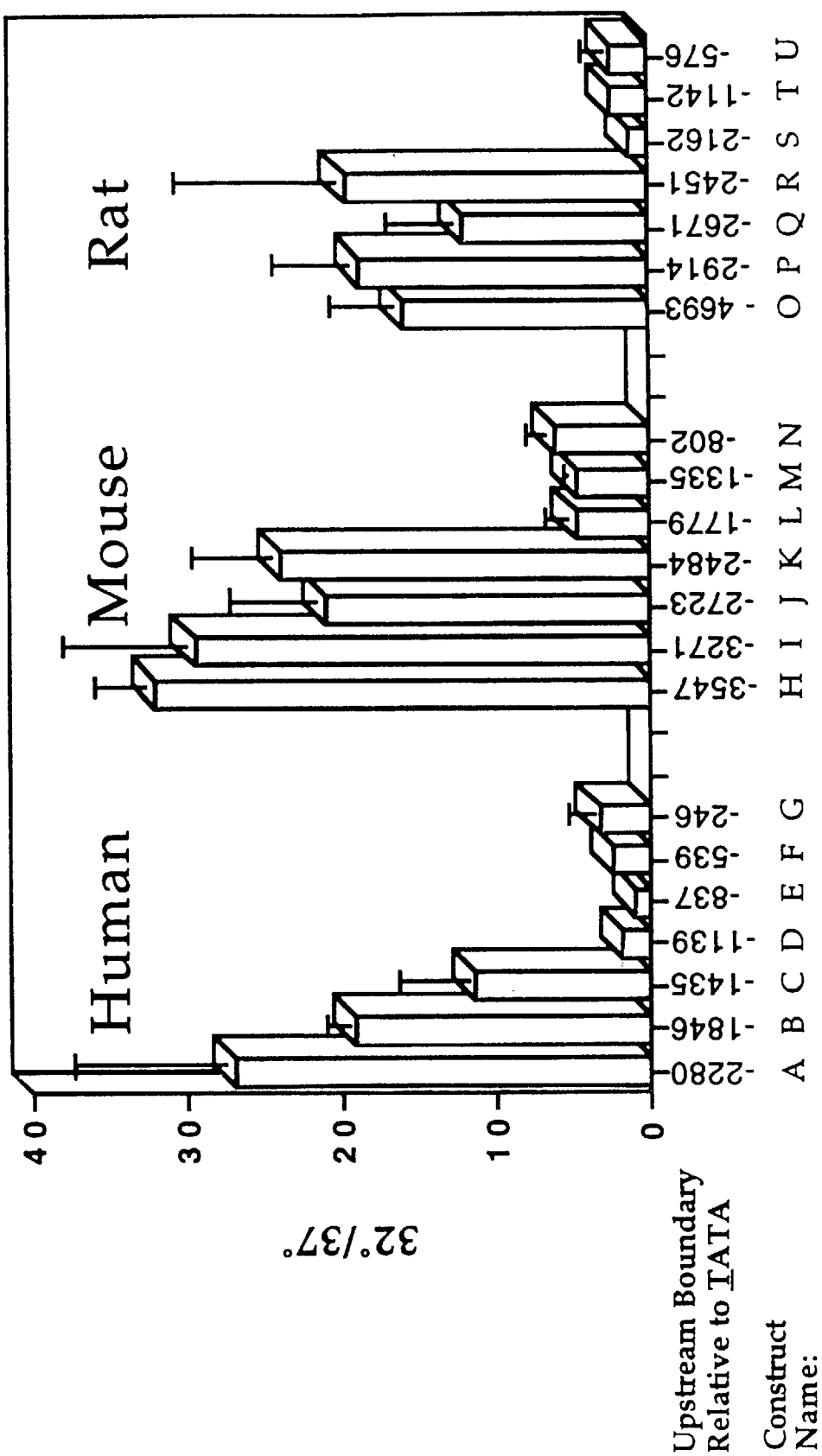

Deletion of Site 1 alone reduced p53 responsiveness in the human constructs, as described previously (El Deiry et al., 1993), but had little effect on the rat and mouse genes (FIG. 1d). However, wt p53 inducibility was largely eliminated when the constructs excluded both Sites 1 and 2 (FIG. 1d, compare constructs C and D in human, K and L in mouse, and R and S in rat). Though it was possible that other sequences between bp 2162 and 2451 (in the rat, for example) mediate p53-responsiveness, the sequence and binding results (FIG. 1b, 1c) strongly suggested that Site 1 is important for p53-inducibility.

Site 3 is of interest in that it contained a palindromic sequence similar to the MyoD recognition site at its 3' end (GACAATGTC). Transcripts of p21$^{WAF1}$ have been shown to be regulated by MyoD in a p53-independent manner (Halevy et al., 1995, Parker et al., 1995). There is strong conservation of the positions of this site with respect to the p53 binding sites in all three species examined (FIG. 1a). Only a few other short stretches of identity among the three species were observed in the upstream sequence comparisons. Of these, the only one with more than 12 bp of contiguous identity is the sequence 5'-AGAATTGTCCTTTAT-3' at position −1067, −1166, and −1245 of the human, mouse, and rat promoters, respectively.

The induction of p21$^{WAF1}$ expression following radiation or chemically induced DNA damage has been shown to be dependent on wt p53 in tissue culture models (El-Deiry et al., 1994, Dulic et al., 1994, Michieli et al., 1994). From a detailed analysis of the upstream regulatory region of p21$^{WAF1}$, it was clear that at least two highly conserved p53-binding sites exist and mediate transcriptional activation of p21$^{WAF1}$ following DNA damage. However, expression of p21$^{WAF1}$ is independent of p53 in other circumstances, such as during the differentiation of leukemia cells following phorbol ester treatment or during the MyoD-dependent formation of myotubes from myoblasts, (Zhang et al., 1995, Halevy et al., 1995, Parker et al., 1995). This p21$^{WAF1}$ expression can be a manifestation of cellular differentiation. The observations in the gastrointestinal tract suggest that p21$^{WAF1}$ expression is not an effect or cause of differentiation per se. Thus, p21$^{WAF1}$ expression is not detected in fully differentiated cells in the bottom half of the crypts, but is expressed in the same cells once they left the replicative compartment and migrated upwards. This suggests that p21$^{WAF1}$ plays a critical role in negatively controlling the proliferative compartment, in line with its known biochemical activities. This inhibition can be required for differentiation to take place in some cell types (e.g., muscle), but the process of differentiation and p21$^{WAF1}$ expression can clearly be separated in the intestine. Site 3 is one attractive candidate for mediate p53-independent regulation of p21$^{WAF1}$. Site 3 is conserved in sequence as well as position relative to p53-binding sites (FIG. 1a, 1b). The complete sequences of the promoters of the human, mouse, and rat genes determined here should facilitate efforts to identify important regulatory features of p21$^{WAF1}$ in the future.

EXAMPLE 5

Immunohistochemical Methods

Paraffin sections were treated with xylene for 30 minutes and hydrated using graded alcohol concentrations. Antigen retrieval was routinely performed on paraffin sections by incubation in prewarmed 100 mM sodium citrate, pH 6.0 at 90° C. for 30 minutes. Frozen sections were fixed for five minutes in Histochoice (Ameresco; Solon, Ohio), followed by incubation in phosphate buffered saline (PBS) for 10 minutes. After blocking nonspecific antigens with filtered goat serum for one hour, frozen or paraffin sections were incubated with primary antibodies for 12 to 16 hours. In some experiments, endogenous peroxidase activity was reduced by treating sections with 3% Hydrogen Peroxide, 50% Methanol in PBS for 5 minutes. Staining was achieved using a Biotin-conjugated goat anti-mouse secondary antibody (Pierce), and the ABC horseradish peroxidase method (Vector laboratories). For double staining, sections were first probed with the anti-Ki67 antibody. Following development of brown nuclear staining with a DAB chromogen (Sigma), sections were treated with 2.2M Glycine, pH 2.0 for one hour. The sections were then blocked with goat serum and probed with anti-p21$^{WAF1}$ antibody. Nickel chloride was added to the chromogen to produce a black staining pattern which was distinguishable from the brown stain of the Ki67 antigen. Tissue specimens were counterstained for 2 minutes in 0.5% methyl green, followed by sequential incubation in 100% ethanol and xylenes then mounted in Cytoseal 60 (Stephens Scientific, Riverdale, N.J.). The ApopTag kit (Peroxidase detection) for in-situ detection of DNA fragmentation was obtained from Oncor (Gaithersburg, Md.) and used as described (Gavrieli et al., 1992).

EXAMPLE 6 p21$^{WAF1}$ Expression in Adult Human Tissues

During the examination of UV-irradiated skin, we noted intense p21$^{WAF1}$ staining in the nucleus of sebaceous glands, whether or not the skin had been irradiated (FIG. 4b). Sebaceous glands are holocrine, that is, they release their contents through total cellular disintegration (Strauss et al., 1991). The proliferating sebaceous cells line the periphery of the gland, and maturing cells can be observed in its center. Staining for p21$^{WAF1}$ was observed in the maturing cells, whereas p53 staining was usually not detectable (FIG. 4a). We suspected that the process of cellular disintegration was a form of apoptosis. This was supported by a terminal deoxynucleotidyl transferase (tdt)-based assay to detect DNA fragmentation in situ (FIG. 4c, 4d).

Figures 6A, 6B, 6C:
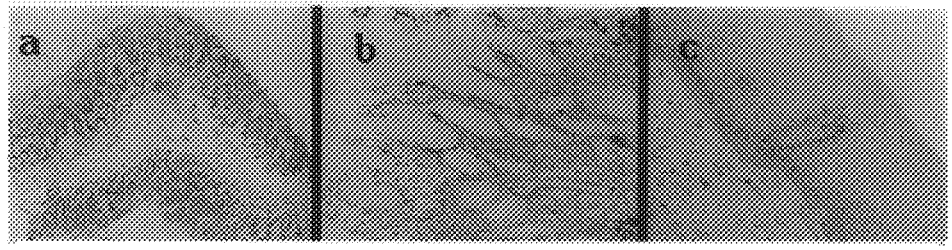
FIG. 6 demonstrates proliferating and nonproliferating compartments in the gastrointestinal tract. Colonic mucosas (FIGS. 6a, 6d, 6g, 6j, and 6k), stomach (FIGS. 6b, 6e, and 6h) and esophagus (FIGS. 6c, 6f, 6i, and 6l) were analyzed for expression of $p21^{WAF1}$ (FIGS. 6a, 6b, 6c, 6d, and 6f), Ki67 (FIGS. 6e, 6g, and 6i), or both $p21^{WAF1}$ (black) and Ki67 (brown) (FIGS. 6h, 6j, 6k, and 6l). Nuclei of cells not expressing Ki67 or $p21^{WAF1}$ are stained green by the counterstain. The non-epithelial cells which appear stained represent tissue macrophages with endogenous peroxidase activity.
Figures 6D, 6E, 6F:
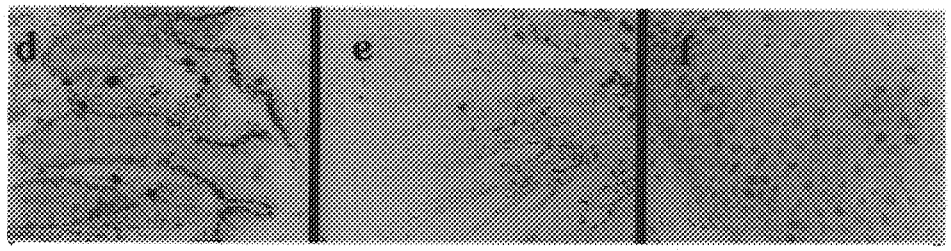

A subset of nuclei in thyroid, prostate, muscle, kidney, breast, testes and gastrointestinal tract epithelia stained intensely for p21$^{WAF1}$ expression, whereas little or no staining was observed in lymph nodes, liver, spleen, brain, heart or lung. There was a striking compartmentalization of p21$^{WAF1}$ expression throughout the gastrointestinal tract. In the colon, for example, p21$^{WAF1}$ staining was confined to the upper half of the crypts (FIG. 6a, 6d). Based on previous studies of crypt cell maturation (Lipkin et al., 1963 a,b), this topography suggested that p21$^{WAF1}$ expression was confined to the post-replicative compartment. Staining the adjacent sections with an antibody reactive with Ki67, a 300 kD nuclear protein which is widely used as a marker of replicating cells (Gerdes et al., 1983, Sawhney and Hall, 1992, Lopez et al., 1994) further confirmed this notion.

Figures 6G, 6H, 6I:
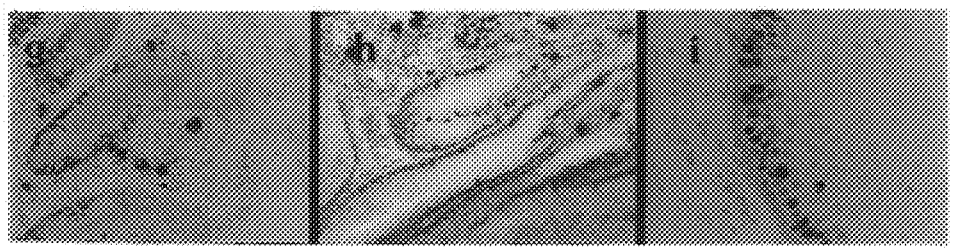
Figures 6J, 6K, 6L:
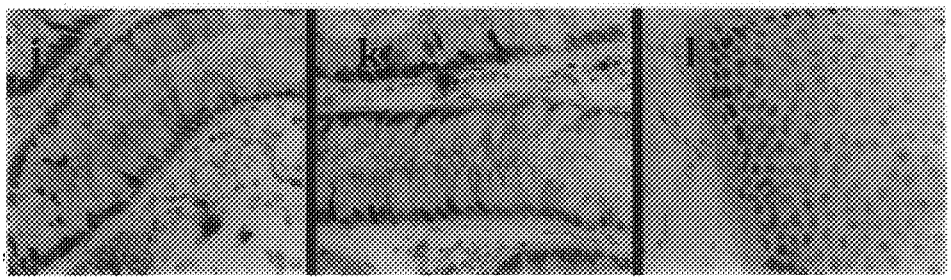

There was a remarkable and mutually exclusive pattern of staining for Ki67 and p21$^{WAF1}$ in gastrointestinal epithelia. In the colon, Ki67 was expressed in cells near the base of the crypt and extended about half way up the crypt columns (FIG. 6g). Ki67 expression then abruptly stopped, and p21$^{WAF1}$ expression began, continuing up to the lumen (FIG. 6d, 6g). Staining of serial sections, as well as double staining of the same section, showed that cells at mid-crypt expressed either Ki67 or p21$^{WAF1}$, but not both (FIG. 6j, 6k). There were a few non-staining cells separating the Ki67 and p21$^{WAF1}$ expressing compartments (FIG. 6j, 6k). No indication of apoptosis was observed in p21$^{WAF1}$-positive cells of the colon by the tdt-based assay.

A few cells at the very base of the crypt also exhibited neither p21$^{WAF1}$ nor Ki67 expression (FIG. 6j). These might represent stem cell reserves, in "Go" phase. The expression of p21$^{WAF1}$ and Ki67 has little relationship to cellular differentiation per se. Fully differentiated mucous secreting goblet cells, for example, express either Ki67 or p21$^{WAF1}$, depending only on their position within the crypt.

A similar inverse relationship between Ki67 and p21$^{WAF1}$ staining was observed in the small intestine. In the oxyntic gastric mucosa, p21$^{WAF1}$ expression was observed in the surface epithelium and the gastric pits (FIG. 6b). Ki67 was expressed in a band-like fashion across the neck of the gastric glands (FIG. 6e). Neither Ki67 nor p21$^{WAF1}$ was expressed in the body of the gastric glands (FIG. 6b, 6e).

Serial sections and double staining indicated that Ki67-and p21$^{WAF1}$ expression in the stomach were mutually exclusive (FIG. 6b, 6e, 6h).

In the stratified squamous epithelium of the esophagus, compartmentalized patterns were also observed. The layer of cells closest to the basement membrane expressed neither p21$^{WAF1}$ nor Ki67 (FIG. 6f, 6i). Most of the cells in the second layer expressed Ki67 but not p21$^{WAF1}$ (FIG. 6i). The next two to three layers expressed p21$^{WAF1}$, but not Ki67 (FIG. 6c, 6f). Serial sections and double staining of esophageal sections revealed the mutually exclusive character of Ki67 and p21$^{WAF1}$ expression (FIG. 6l).

In contrast to p21$^{WAF1}$, there was no p53 expression detectable at the immunohistochemical level in gastrointestinal tract epithelia. This suggests that the observed p21$^{WAF1}$ expression is not dependent on p53 expression. p21$^{WAF1}$ expression was examined in normal mice and in p53-null animals generated by homologous recombination. Colonic crypt epithelium was isolated using a physical fractionation technique from p53 −/− and +/+ animals and probed for p21$^{WAF1}$ expression by Northern blot analysis (FIG. 7). Colonic epithelium was prepared by scraping the colonic lumen of mice with a rubber policeman ten minutes after incubation in Hank's Balanced Salt Solution containing 30 mM EDTA. Phase microscopy demonstrated that over 98% of the scraped cells consisted of epithelium. Total cellular RNA was isolated from the crypts and Northern blot analysis was performed as previously described (El-Deiry et al., 1993). A 2.0 kb mouse p21$^{WAF1}$ cDNA was used as the probe following random primer labeling (Feinberg and Vogelstein, 1983). The expression of p21$^{WAF1}$ in such crypt cells was similar in the normal and p53-null mice, consistent with recent in situ hybridization results (Parker et al., 1995).

EXAMPLE 7 p21$^{WAF1}$ Expression in Tumors

Figures 8A, 8B, 8C, 8D, 8E, 8F:
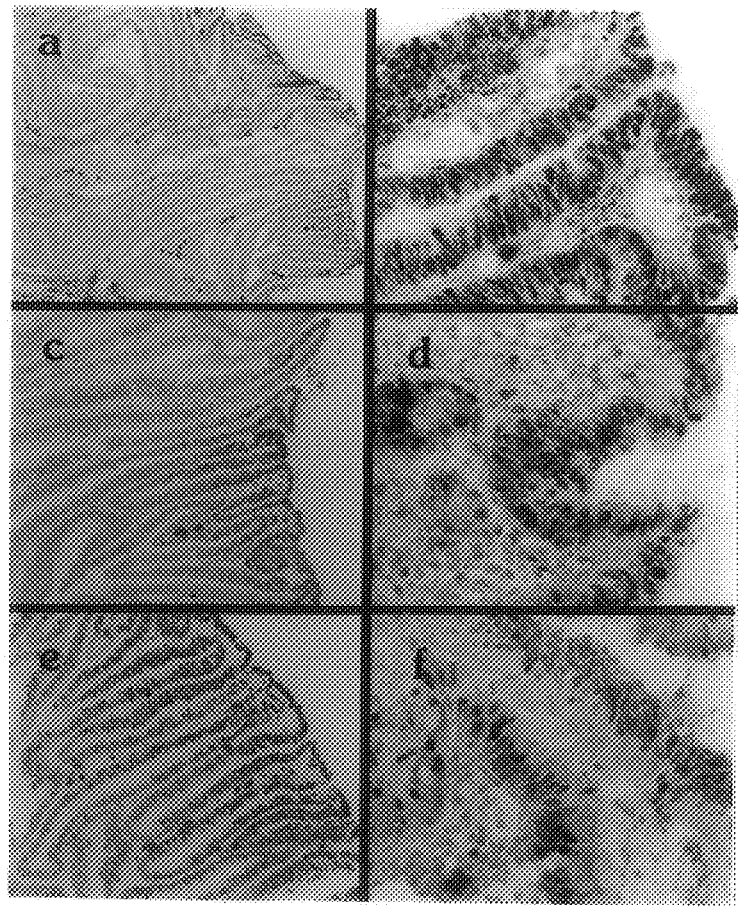
FIG. 8a shows a low power view (40×) of the $p21^{WAF1}$-expressing portion of an adenoma stained with the EA10 monoclonal antibody.
FIG. 8c shows a higher power view (100×) of the same adenoma. Ki67 staining of a serial section from the same adenoma is shown in FIG. 8e (100× magnification). Double staining of this adenoma with Ki67 (brown) and $p21^{WAF1}$ (black) is shown in FIG. 8b at 400× magnification. The $p21^{WAF1}$ expressing portions of two other adenomas, double stained for Ki67 and $p21^{WAF1}$ expression, are shown in FIGS. 8d and 8f (400× magnification). The non-epithelial cells which appear stained represent tissue macrophages with endogenous peroxidase activity.

We next determined whether the normal pattern of p21$^{WAF1}$ expression was preserved in colorectal adenomas. Adenomas are benign tumors representing the early stages of neoplasia (Fearon and Vogelstein, 1990). The crypts of these tumors, though composed of cells which often differentiated and migrated in normal fashion, had abnormal patterns of p21$^{WAF1}$ expression in two respects. First, there was a global decrease in p21$^{WAF1}$ expression. In normal colon, virtually every cell in the top half of each crypt stained intensely for p21$^{WAF1}$ (FIG. 6a). In tumors such as adenomas, which are benign tumors representing the early stages of neoplasia (Fearon and Vogelstein, 1990), less than 20% of the crypts had any observable p21$^{WAF1}$ expression, and in those that did, the expression was confined to cells near the surface (FIG. 8a). However the crypts of these tumors are composed of cells which often differentiate and migrate in normal fashion. Second, the distinct separation between Ki67 and p21$^{WAF1}$ expressing compartments observed in normal tissues such as colonic epithelium was abrogated in tumors such as adenomas. Serial sections and double staining for p21$^{WAF1}$ and Ki67 demonstrated a seemingly random mix of p21$^{WAF1}$ and Ki67 expressing cells at the surface of the adenomatous crypts (FIG. 8b). The abnormal pattern of p21$^{WAF1}$ expression observed in the benign tumors is not a result of p53 mutation, as no p53 expression was observed in these adenomas, including the cells expressing p21$^{WAF1}$. High p53 expression would be expected if p53 mutations existed (Rodrigues et al., 1990, Levine et al., 1991). The immunohistochemical data on p53 are consistent with previous sequencing studies, which showed that p53 mutations are rare in adenomas (Baker et al., 1990). Each of six adenomas from six different patients exhibited the same disorganized patterns (examples in FIG. 8). The altered pattern of p21$^{WAF1}$ expression in the adenomas is not simply a manifestation of increased crypt length, as the elongated regenerating crypts found in patients with ulcerative colitis revealed a normal compartmentalization of p21$^{WAF1}$ and Ki67-expression cells.

Figures 9A, 9B, 9C:
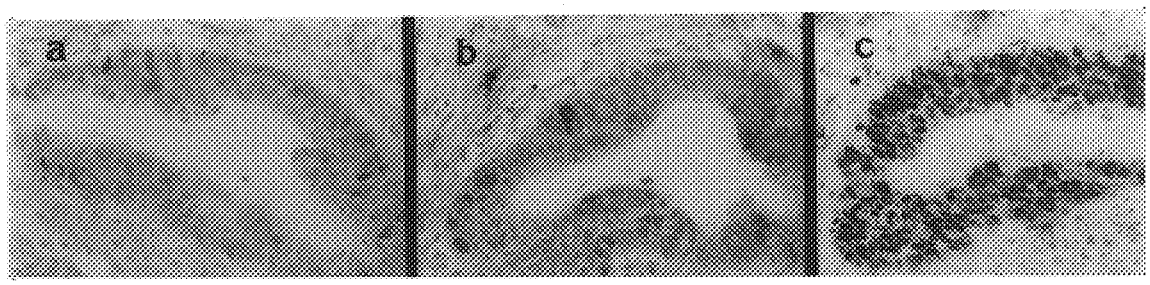
FIG. 9 demonstrates patterns of $p21^{WAF1}$ and p53 expression in malignant colonic tumors. Coincident p53 and $p21^{WAF1}$ expression was observed in a portion of the colorectal carcinoma shown in FIGS. 9a, 9b, and 9c. This tumor contained wild-type p53. Prominent p53 expression without detectable $p21^{WAF1}$ expression was observed in two colorectal cancers with p53 mutation (one in FIGS. 9d, 9e, 9f, and the other in FIGS. 9g, 9h, and 9i). Expression of $p21^{WAF1}$ was observed in some of the stromal cells in FIG. 9e, but not in the neoplastic epithelium. The anti-p53 antibody was used in FIGS. 9a, 9d, and 9g, the anti-$p21^{WAF1}$ antibody was used in FIGS. 9b, 9e, and 9h, and the anti-Ki67 antibody was used in FIGS. 9c, 9f, and 9i. The non-epithelial cells which appear stained represent tissue macrophages with endogenous peroxidase activity.
Figures 9D, 9E, 9F:
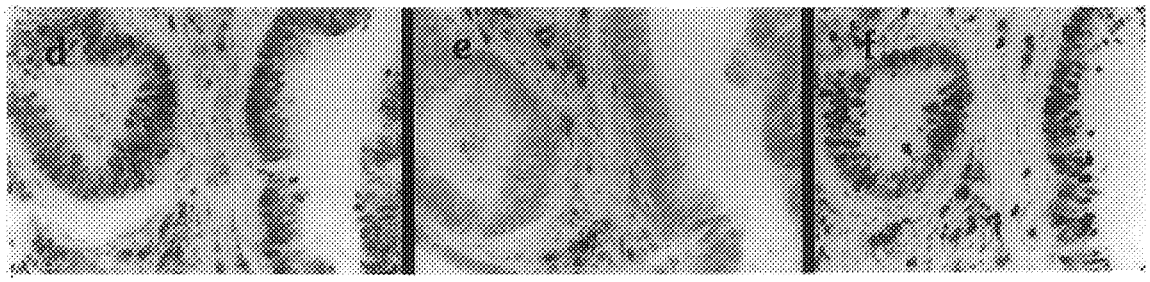
Figures 9G, 9H, 9I:
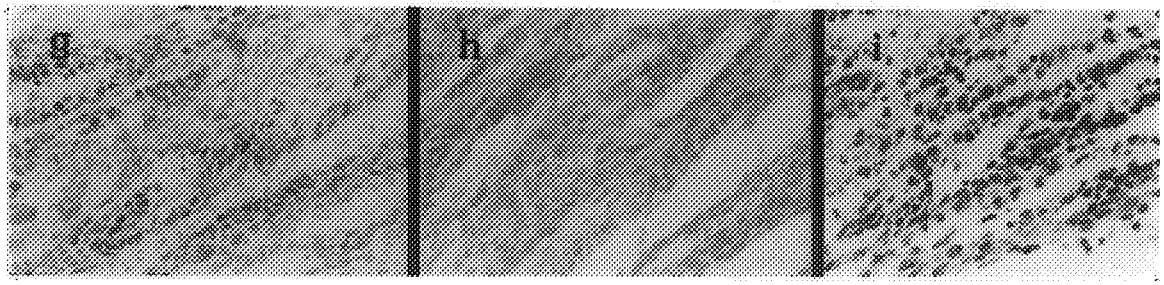

Neoplasms in the advanced stage represented by five malignant colorectal tumors, one with wild-type p53 and four with mutations ($175^{arg>his}$, $220^{try>cys}$, $248^{arg>gln}$, $286^{glu>lys}$; Baker et al., 1990) were also examined. In such advanced neoplasms, crypts with defined bases and lumens were not observed, but gland-like structures composed of malignant epithelium infiltrate the layers of the colonic wall. In the colorectal carcinoma with wt p53, neither p21$^{WAF1}$ nor p53 expression could be observed in the majority of the epithelial cells (as in most adenoma cells). However, a subset of glands expressed both p21$^{WAF1}$ and p53 (FIG. 9a, 9b). Serial sections revealed that the same cells expressed both p21 and p53, suggesting that the former was dependent on the latter. In the four colorectal cancers with p53 mutations, high levels of p53 were observed, as expected, but low or undetectable p21$^{WAF1}$ expression was found (examples in FIG. 9d, 9e, 9g, 9h). Ki67 was found to be expressed throughout the cancers, regardless of p53 status (FIG. 9C, 9f, 9i).

A related point concerns the topological organization of p21$^{WAF1}$ expression, a phenomenon which can not have been appreciated from cell culture studies. The striking distribution of p21$^{WAF1}$ expression in colonic crypts and squamous epithelium suggests that cell-cell or cell-stroma interactions is contributing to cell cycle control. As cells migrate up the crypt, they make contacts which influence the replicative machinery negatively (loss of Ki67 expression) as well as positively (induction of p21$^{WAF1}$). In colonic neoplasms, there is a disorganization of this precisely ordered topological relationship between cycling and cycle-inhibited cells. This form of molecular disorganization occurs quite early in the neoplastic process, as it is present in benign adenomas, long before malignant transformation.

This is consistent with a two-stage model for the abrogation of cell cycle control in neoplasia. The first stage involves a loss of the highly ordered spatial separation between proliferating and nonproliferating compartments. In the case of colonic adenomas, this could be due to mutations in the APC gene (Powell et al., 1992), which could result in disruption of cell contact signaling of growth as cells migrate up the crypts. APC normally is expressed at higher levels as cells travel up the crypt (Smith et al., 1993), and influences the cadherin-catenin network linking cell-cell contacts to the cytoskeleton (Rubinfeld et al., 1993, Su et al., 1993). As tumors progress towards more malignant forms, other signals in the abnormal microenvironment could induce wt p53 expression with consequent p21$^{WAF1}$ induction. Such abnormal microenvironments could be present in the subset of glands in the wild type p53 containing cancers that exhibit coincident p53 and p21$^{WAF1}$ expression (FIG. 9a, 9b). The p53 gene could function in these circumstances as a kind of "emergency brake," checking further uncontrolled proliferation. However, once p53 is induced in this way, the stage is set for selective outgrowth of a p53-mutant cell, relieving the final check on cell cycle control (FIGS. 9d 9e, 9g, 9h). In summary, there is a precisely ordered topological pattern of p21$^{WAF1}$ expression in normal cells which becomes disordered during neoplasia. It is expect that other CDK inhibitors will be analogously affected in specific neoplasms, and that their topographic analysis will provide a new dimension to the study of naturally occurring tumors.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

BIBLIOGRAPHY

Baker, S. J. 1 Preisinger, A. C., Jessup, J. M., Paraskeva, C., Markowitz, S., Willson, J. K. V., Hamilton, S., and Vogelstein, B. (1990). p53 gene mutations occur in combination with 17p allelic deletions as late events in colorectal tumorigenesis. Cancer Res. 50, 7717–7722.

Bulirich, F., MacLachlan, T. K., Sang, N., Druck, T., Veronese, M. L., Alien, S. L., Chiorazzi, N., Koff, A., Heubner, K., Croce, C. M., and Giordano, A. (1995). Chromosomal mapping of members of the cdc2 family of protein kinases, cdk3, cdk6, PISSLRE, and PITALRE, and a cdk inhibitor, P27KiP1, to regions involved in human cancer. Cancer Res. 55, 1199–1205.

Campbell, C., Quinn, A. G., Angus, B., Farr, P. M., and Rees, J. L. (1993). Wavelength specific patterns of p53 induction in human skin following exposure to ultraviolet radiation. Cancer Res. 53, 2697–2699.

Devine, S. E., and Boeke, J. D. (1994). Efficient integration of artificial transposons into plasmid targets in vitro: a useful tool for DNA mapping, sequencing and genetic analysis. Nucleic Acids Res. 22, 3765–3772.

Dulic, V., Kaufmann, W. K., Wilson, S. J., Tlsty, T. D., Lees, E., Harper, J. W., Elledc,e, S. J., and Reed, S. I. (1994). p53-dependent inhibition of cyclin-dependent kinase activities in human fibroblasts during radiation-induced G1 arrest. Cell 76, 1013–1024.

El-Deiry, W. S., Kern, S. E., Pietenpol, J. A., Kinzler, K. W., and Vogelstein, B. (1992). Definition of a consensus binding site for p53. Nature Genet. 1, 45–49.

El-Deiry, W. S., Tokino, T., Velculescu, V. E., Levy, D. B., Parsons, R., Trent, J. M., Lin, D., Mercer, W. E., Kinzler, K. W., and Vogelstein, B. (1993). WAF1, a potential mediator of p53 tumor suppression. Cell 75, 817–825.

El-Deiry, W. S., Harper, J. W., O'Connor, P. M., et al. (1994). WAF1/CIP1 is induced in p53-mediated G1 arrest and apoptosis. Cancer Res. 54, 1169–1174.

Fearon, E. R., and Vogelstein, B. (1990). A genetic model for colorectal tumorigenesis. Cell 61, 759–767.

Feinberg, A. P., and Vogelstein, B. (1983). A technique for radiolabeling DNA restriction endonuclease fragments to high specific activity. Anal. Biochem. 132, 6–13.

Flores-Rozas, H., Kelman, Z., Dean, F. B., Pan, Z. Q., Harper, J. W., Elledge, S. J., O'Donnell, M., and Hurwitz, J. (1994). Cdk-interacting protein 1 directly binds with proliferating cell nuclear antigen and inhibits DNA replication catalyzed by the DNA polymerase delta holoenzyme. Proc. Natl. Acad. Sci. USA 91, 8655–8659.

Fridovich-Keil, J. L., Gudas, J. M., Bryan, I. B., and Pardee, A. B. (1991). improved expression vectors for eukaryotic promoter/enhancer studies. Biotechniques 11, 572–579.

Funk, W. D., Pak, D. T., Karas, R. H., Wright, W. E., and Shay, J. W. (1992). A transcriptionally active DNA-binding site for human p53 protein complexes. Mol. Cell. Biol. 12, 2866–2871.

Gavrieli, Y., Sherman, Y., and Ben-Sasson, S. A. (1992). Identification of programmed cell death in situ via specific labeling of nuclear DNA fragmentation. J. Cell Biol. II 9, 493–501.

Gerdes, J., Schwab, U., Lemke, H., and Stein, H. (1983). Production of a mouse monoclonal antibody reactive with a human nuclear antigen associated with cell proliferation. Int. J. Cancer 31, 13–20.

Gerdes, J., Lemke, H., Baisch, H., Wacker, H. -H., Schwab, U., and Stein, H. (1984). Cell cycle analysis of a cell proliferation-associated human nuclear antigen defined by the monoclonal antibody Ki67. J. Immunol. 133, 1710–1715.

Gu, Y., Turck, C. W., Morgan, D. O. (1993). Inhibition of CDK2 activity in vivo by an associated 20K regulatory subunit. Nature 366, 707710.

Guan, K. -L., Jenkins, C. W., Li, Y., Nichols, M. A., Wu, X., O'Keefe, C. L., Matera, A. G., and Xiong, Y. (1994). Growth suppression by p18, a p16$^{INK4/MTS1}$-and p14$^{INK4B/MTS2}$-related CDK6 inhibitor, correlates with wild-type pRb function. Genes and Dev. 8, 29392952.

Halevy, O., Novitch, B. G., Spicer, D. B., Skapek, S. X., Rhee, J., Hannon, G. J., Beach, D., and Lassar, A. B (1995). Correlation of terminal cell cycle arrest of skeletal muscle with induction of p21 by MyoD Science 67, 1018–1021.

Hannon, G. J., Beach, D. (1994). p15$^{INK4B}$ is a potential effector of TGF-b-induced cell cycle arrest. Nature 371, 257–261.

Harper, J. W., Adami, G. R., Wei, N., Keyomarsi, K, Enedge, S. J. (1993). The p21 cdk-interacting protein Cip1 is a potent inhibitor of G1 cyclin-dependent kinases. Cell 75, 805–816.

Hunter, T., and Pines, J. (1994). Cyclins and Cancer. II: Cyclin D and CDK inhibitors come of age. Cell 79, 573–582.

Hussussian, C. J., Struewing, J. P., Goldstein, A. M., Higgins, P. A., Ally, D. S., Sheehan, M. D., Clark, W. H., Jr., Tucker, M. A., and Dracopoli, N. C. (1994). Germline p16 mutations in familial melanoma. Nature Genet. 8, 15–21.

Jen, J., Harper, J. W., Bicner, S. H., Bigner, D. D., Papadopoulous, N., Markowitz, S., Willson, J. K. V., Kinzler, K. W., and Vogelstein, B. (1994). Deletion of p16 and p15 genes in brain tumors. Cancer Res. 54, 6353–6358.

Kamb, A., Gruis, N. A., Weaver-Feldhaus, J. et al. (1994a). A cell cycle regulator potentially involved in genesis of many tumor types. Science 264, 436–440.

Kamb, A., Shattuck-Eidens, D., Eeles, R. et al. (1994b). Analysis of the p16 gene (CDKN2) as a candidate for the chromosome 9p melanoma susceptibility locus. Nature Genet. 8, 23–26.

Kastan, M. B., Zhan, Q., El-Deiry, W. S., Carrier, F., Jacks, T., Walsh, W. V., Plunkett, B. S., Vogelstein, B., and Fornace, Jr., A. J. (1992). A mammalian cell cycle checkpoint pathway utilizing p53 and GADD45 is defective in ataxia-telangiectasia. Cell 71, 587–597.

Kern, S. E., Pietenpol, J. A., Thiagalingam, S., Seymour, A., Kinzler, K. W., and Vogelstein, B. (1992). Oncogenic forms of p53 inhibit p53 regulated gene expression. Science 256, 827–830.

Levine, A. J., Momand, J., and Finlay, C. A. (1991). The p53 tumour suppressor gene. Nature 351, 453–456.

Li, R., Waga, S., Hannon, G. J., Beach, D., and Stillman, B. (1994). Differential effects by the p21 CDK inhibitor on PCNA-dependent DNA replication and repair. Nature 371, 534–537.

Lipkin, M., Bell, B., and Sherlock, P. (1963a). Cell proliferation kinetics in the gastrointestinal tract of man. I. Cell renewal in colon and rectum. J. Clin. Invest. 42, 767.

Lipkin, M., Sherlock, P., and Bell, B. (1963b). Cell proliferation kinetics in the gastrointestinal tract of man. II. Cell renewal in stomach, ileum, colon, and rectum. Gastroenterology 45, 721.

Lopez, F., Belloc, F., Lacombe, F., Dumain, P., Reiffers, J., Bernard, P., and Boisseau, M. R. (1994). The labeling of proliferating cells by Ki67 and MIB-1 antibodies depends on the binding of a nuclear protein to the DNA. Exp. Cell Res. 210, 145–153.

Lu, X., and Lane, D. P. (1993). Differential induction of transcriptionally active p53 following uv or ionizing radiation: defects in chromosome instability syndromes? Cell 75, 765–778.

Mercer, W. E., Shields, M. T., Amin, M., Sauve, G. J., Appella, E., Romano, J. W., and Ullrich, S. J. (1990). Negative growth regulation in a glioblastoma tumor cell line that conditionally expresses wild-type p53. Proc. Natl. Acad. Sci. USA 87, 6166–6170.

Michalovitz, D., Halevy, O., and Oren, M. (1990). Conditional inhibition of transformation and of cell proliferation by a temperature-sensitive mutant of p53. Cell 62, 671–680.

Michieli, P., Chedid, M., Lin, D., Pierce, J. H., Mercer, W. E., and Givol, D. (1994). Induction of WAF1/C1P1 by a p53-independent pathway. Cancer Res. 54, 3391–3395.

Nobori, T., Miura, K., Wu, D. J., Lois, A., Takabayashi, K., and Carson, D. A. (1994). Deletions of the cyclin-dependent kinase-4 inhibitor gene in multiple human cancers. Nature 368, 753–756.

Noda, A., Ning, Y., Venable, S. F., Pereira-Smith, O. M., Smith, J. R. (1994). Cloning of senescent cell-derived inhibitors of DNA synthesis using an expression screen. Exp. Cell Res. 211, 90–98.

Parker, S. B., Eichele, G., Zhang, P., Rawls, A., Sands, A. T., Bradley, A., Olson, E. N., Harper, J. W., and Elledge, S. J. (1995). p53-independent expression of p21$^{CiP1}$ in muscle and other terminally differentiating cells. Science 267, 1024–1027.

Pietenpol, J. A., Bohlander, S. K., Sato, Y., Papadopoulos, N., Liu, B., Friedman, C., Trask, B. J., Roberts, J. M., Kinzler, K. W., Rowley, J. D., and Vogelstein, B. (1995). Assignment of the human p27$^{KiP1}$ gene to 12p 13 and its analysis in leukemias. Cancer Res. 55, 1206–1210.

Polvak, K. Lee, M. -H., Erdjument-Bromace, H., Koff, A., Tempst, P., Roberts, J. M., Massagu, J. (1994). Cloning of p27$^{KiP1}$, a cyclin-cdk inhibitor and a potential mediator of extracellular antimutagenic signals. Cell 78, 59–66.

Ponce-Castaneda, M. V., Lee, M. -H., Latres, E., Polyak, K., Lacombe, L., Montgomery, K., Mathew, S., Krauter, K., Sheinfeld, J., Massague, J., and Cordon-Cardo, C. (1995). p27KiPI: Chromosomal mapping to 12p12–12p13.1 and absence of mutations in human tumors. Cancer Res. 55, 1211–1214.

Powell, S. M., Zilz, N., Beazer-Barclay, Y., Bryan, T. M., Hamilton, S. R., Thibodeau, S. N., Vogelstein, B., and Kinzler, K. W. (1992). APC mutations occur early during colorectal tumorigenesis. Nature 359, 235–237.

Rodrigues, N. R., Rowan, A., Smith, M. E. F., Kerr, I. B., Bodmer, W. F., Gannon, J. V., and Lane, D. P. (1990). p53 mutations in colorectal cancer. Proc. Natl. Acad. Sci. USA 87, 7555–7559.

Rubinfeld, B., Souza, B., Albert, I., Muller, O., Chamberlain, S. H., Masiarz, F. R., Munemitsu, S., and Polakis, P. (1993). Association of the APC gene product with beta-catenin. Science 262, 1731–1734.

Sawhney, N., and Hall, P. A. (1992). Ki67-structure, function, and new antibodies. J. Pathol. 168, 161–162.

Serrano, M., Hannon, G. J., Beach, D. (1993). A new regulatory motif in cell cycle control causing specific inhibition of cyclin D/CDK4. Nature 366, 704-70-1.

Sherr, C. J. (1994). G1 phase progression: cycling on cue. Cell 79, 551–555.

Smith, K. J., Johnson, K. A., Bryan, T. M., et al. (1993). The APC gene product in normal and tumor cells. Proc. Natl. Acad. Sci., U.S.A. 90, 2846–2850.

Strauss, J. S., Downing, D. T., Ebling, F. J., Stewart, M. (1991). Sebaceous glands. In Physiol., Biochem., and Molec. Biol. of the Skin, L. A. Goldsmith, ed., Oxford Univ. Press, p-712.

Su, L. -K., Vogelstein, B., and Kinzler, K. W. (1993). Association of the APC tumor suppressor protein with catenins. Science 262, 1734–1737.

Toyoshima, H., Hunter, T. (1994). p27, a novel inhibitor of G1 cyclin-Cdk protein kinase activity, is related to p21. Cell 78, 67–74.

Xiong, v., Zhang, H., and Beach, D. (1993a). Subunit rearrangement of the cyclin-dependent kinases is associated with cellular transformation. Genes and Dev. 7, 1572–1583.

Xiong, Y., Hannon, G. J., Zhangy H., Casso, D., Kobayashi, R., Beach, D. (1993b). p21 is a universal inhibitor of cyclin kinases. Nature 366, 701–704.

Xiong, Y., Zhang, H., and Beach, D. (1992). D type cyclins associate with multiple protein kinases and the DNA replication and repair factor PCNA. Cell 71, 505–514.

Zhang, W., Grasso, L., McClain, C. D., Gambel, A. M., Cha, Y., Travali, S., Deisseroth, A. B., and Mercer, W. E. (1995). p53-independent induction of WAF1/CIP1 in human leukemia cells is correlated with growth arrest accompanying monocyte/macrophage differentiation. Cancer Res. 55, 668–674.

We claim:

1. An in vitro method for expressing a gene in a cell which expresses p21$^{WAF1}$ comprising the step of:

administering to the cell a nucleic acid construct comprising a p21$^{WAF1}$ transcription regulatory region operably linked in a cis configuration to the gene, whereby the gene is expressed in the cell.

2. The method of claim 1 wherein the p21$^{WAF1}$ transcription regulatory region comprises a sequence selected from the group consisting of nucleotides 1–15 of SEQ ID NO: 3, nucleotides 1–36 of SEQ ID NO: 4, nucleotides 1–20 of SEQ ID NO: 5, and nucleotides 1–33 of SEQ ID NO: 6.

3. The method of claim 1 wherein the p21$^{WAF1}$ transcription regulatory region comprises nucleotides 1–5143 of SEQ ID NO: 7.

4. The method of claim 1 wherein the p21$^{WAF1}$ transcription regulatory region comprises nucleotides 17–36 of SEQ ID NO: 4.

* * * * *